United States Patent [19]
Raines

[11] Patent Number: 6,149,587
[45] Date of Patent: *Nov. 21, 2000

[54] INTEGRATED, PERIPHERAL VASCULAR DIAGNOSTIC SYSTEM AND METHOD THEREFOR

[75] Inventor: Jeffrey K. Raines, Coral Gables, Fla.

[73] Assignee: Vasocor, Inc., Miami, Fla.

[*] Notice: This patent is subject to a terminal disclaimer.

[21] Appl. No.: 09/470,040

[22] Filed: Dec. 22, 1999

Related U.S. Application Data

[63] Continuation of application No. 08/968,910, Nov. 6, 1997, Pat. No. 6,017,307, which is a continuation of application No. 08/662,438, Jun. 10, 1996, abandoned.
[60] Provisional application No. 60/018,784, May 31, 1996.

[51] Int. Cl.⁷ .......................................................... A61B 5/02
[52] U.S. Cl. ............................................................. 600/300
[58] Field of Search ..................................... 600/300–301, 600/438, 483–484; 128/878, 903, 920–924

[56] References Cited

U.S. PATENT DOCUMENTS

| | | | |
|---|---|---|---|
| 4,509,526 | 4/1985 | Barnes et al. | 128/663 |
| 5,050,613 | 9/1991 | Newman et al. | 128/670 |
| 6,017,307 | 1/2000 | Raines | 600/300 |

FOREIGN PATENT DOCUMENTS

WO 94/24929  11/1994  WIPO.

Primary Examiner—Cary O'Connor
Assistant Examiner—Ryan Carter
Attorney, Agent, or Firm—Robert C. Kain, Jr.; Fleit Kain Gibbons

[57] ABSTRACT

The integrated peripheral vascular diagnostic system electronically links a pulse volume recorder PVR, an ocular pneumoplethysmograph OPG, a photoplethysmograph PPG, an audio-frequency analyzer AA unit which characterizes blood flow with a sensitive microphone, and a doppler ultrasound unit. This diagnostic equipment generates data signals. These data signals are converted into digital data signals and are stored in a database. The diagnostic system includes a computer with a processor, a memory, a keypad input device, a display monitor, a printer and an interface for connecting these electronic components together along with an interface for the PVR, OPG, PPG, AA and doppler ultrasound. The diagnostic system further includes a report generator which generates, displays and prints a plurality of vascular diagnostic reports from the digital instrument data signals and the keypad entry data. The diagnostic system also includes, in a further embodiment, an audio playback device such that the technician, when preparing the vascular diagnostic report, can listen to analog versions of the digital instrument data signals. The method for electronically integrating the vascular diagnostic system includes electronically obtaining and converting the instrument data signals into digital data signals, inputting keypad entry data representing manually acquired vascular medical data from the patient, compiling the digital data and the keypad entry data into a database and generating, displaying and printing a plurality of vascular diagnostic reports.

43 Claims, 39 Drawing Sheets

Arterial Evaluation – Lower Extremities

Patient Information

Name: St., Peter L          Date: 5/30/96
SSN/ID: 267-,     Sex: M   Age: 33   Date of Prior Evaluation:    New
Referring Physician: Nichols           Examined By: B K

Vascular History

Cigarette Smoking: Current        Hypertension: N        Diabetic: Oral (1)
Hyperlipidemia: 2        Obesity: N        Angina: 3        MI: N        CVA: N
Vascular Skin Lesions: None
Resting Symptoms: None
Exertional Symptoms: Complains of Right Calf pain on walking approximately one (1) block
S/P and Notes:
1 – Required only over last 2 months
2 – Mild elevation in LDL
3 – Requires Nitroglycerin several times per week Brachial Blood Pressure: 140/85        Arm: (L)eft/(R)ight: R

Arterial Pulse

|  |  | Femoral | Popliteal | Anterior Tibial | Posterior Tibial | Femoral Bruits |
|---|---|---|---|---|---|---|
| Pulses | Left | 3 | 3 | 3 | 3 | ☐ |
|  | Right | 3 | 3 | 3 | 3 |  |
| Doppler Signal | Left | ✓ | ✓ | ✓ | ✓ | ✓ normal |
|  | Right | ✓ | ✓ | ✓ | ✓ | ↓ reduced<br>o absent |

*FIG. 15*

Arterial Evaluation – Lower Extremities

Exercise Evaluation

Maximum Walking Time (min) [5.0]   Rate (mph) [1.5]   Grade (%) [10.0]

Symptoms at [1.0] minute(s)  None

Symptoms at [2.0] minute(s)  None

Symptoms at [4.0] minute(s)  Localized Right Calf Discomfort

Symptoms with Exercise  At 4.0 minutes the subject complained of localized Right Calf discomfort. There was no extension and the symptom did not increase. Exercise was terminated at 5 minutes.

POST-EXERCISE SEGMENTAL PULSE VOLUME AND PRESSURE DATA

Brachial Systolic Pressure (mmHg) [140]        Femoral Bruits  Right ☐   Left ☐

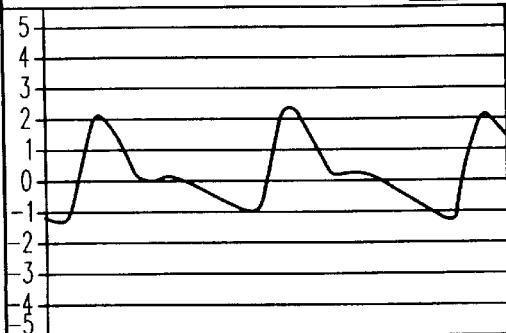

RIGHT ANKLE     Psys [135] mmHg         LEFT ANKLE     Psys [135] mmHg
Ankle/Arm Index [0.96]                  Ankle/Arm Index [0.96]

*FIG. 18*

Arterial Evaluation Lower Extremities

Arterial Evaluation
Lower Extremities

Arterial Evaluation Lower Extremities

Residual Lumen/ Calcification

Soft Plaque

Smooth Margins

Irregular Margins

Ulceration Margins

Absorption

Male Impotence

Patient Information
Name: Ni, Michael J  Date: 5/30/96
SSN/ID: 590-  Sex: M  Age: 38  Date of Prior Evaluation: New
Referring Physician: Reese  Examined By: RK

Vascular History
| | | | | | | | |
|---|---|---|---|---|---|---|---|
| Cigarette Smoking | Non | Hypertension | Y | Diabetic | Insulin-1 | | |
| Hyperlipidemia | N | Obesity | N | Angina | N | MI 3 | CVA N |

Vascular Skin Lesions: None
Resting Symptoms: None
Exertional Symptoms: None

S/P and Notes
1 - Insulin dependent for 15 years.

Brachial Blood Pressure: 120 / 80    Arm: (L)eft/(R)ight R

Surgical Proceedures
| Proceedure Name | Proceedure Date |
|---|---|
| Right Hernia Repair | 23-Jan-90 |

Medications
| Medication Name | Dosage | When Taken |
|---|---|---|
| Insulin | 40 units | Daily |

*FIG. 23*

History

1. Describe the problem you are having with sexual function:
   `Difficult in maintaining penile erection.`

2. Do you have problems ☐ (obtaining) or ☑ (maintaining) an erection or
   ☐ (both) or ☐ (neither) ?

Presently, what is the average grade of your erection? `3` (0 - no erection.... 10 - full erection)

3. When did you first notice the change in sexual function? `6/1/95` (month/year)

4. Was the change of ☐ (gradual) or ☑ (rapid) onset ?

5. Do you recall any other significant events which occurred around the same time?
   (partner/marital problems, loss of job, death in family, other illnesses, etc.)
   `None`

6. Do you have an (erection) or (semi-erection) in the morning upon awakening? ☑ Yes ☐ No
   How often `Weekly`     Grade `3`

7. Do you ever awaken at night and notice an erection or semi-erection? ☐ Yes ☑ No
   How often `        `     Grade `  `

8. Do other types of stimulus improve your erections? ☑ Yes ☐ No     Grade `4`
   ☑ (Masturbation) ☐ (Oral Sex) ☐ (Erotic films) ☐ (Reading material)

9. Are your erections ever sufficient for penetration ☑ Yes ☐ No
   How often? `50%`

10. Do you notice any ☐ (increase) ☐ (decrease) ☑ (no change)
    in your erection with position changes?  If yes, explain:
    `                                                        `

11. Have you noticed any change in the appearance or shape of your penis?
    ☑ (curvature) ☐ (color change) ☐ (lumps) ☐ (no change)  Date noticed `Slight bend n`
    Explain: `6/30/95`

12. When was the last time you had successful intercourse? `5/20/96`

*FIG. 24*

13. Are you able to ejaculate?  ☑ Yes  ☐ No
    By what method:  ☑ (intercourse)  ☑ (Oral sex)  ☑ (Masturbation)
    Does the semen:  ☐ (spurt out) ☑ (flow out slowly) ☐ (retrograde - goes back into the bladder)

14. Do you have a premature ejaculation?  ☐ Yes  ☑ No
    If yes, has it been ☐ (lifelong) or ☐ (recent) onset  ☐ Date [                ]

15. Do you consider your libido (sexual desire) normal?  ☑ Yes  ☐ No
    If no, since when [2 - 3 months ago        ]

16. Do you have a (decrease in sensation) of the penis or (complete numbness) of the penis?
    ☐ Yes  ☑ No    Date noticed [            ]

17. Has sexual dysfunction affected your relationship with your partner?
    ☐ Yes  ☑ No    If yes, how [                                    ]

18. Have you and/or your partner received any treatment or counseling for this problem?
    ☐ Yes  ☑ No    Explain  [                                       ]

19. Are you having any bladder problems:   Frequency during day?      ☐ Yes  ☑ No
                                            Frequency during night?    ☐ Yes  ☑ No
                                            Urgency?                   ☐ Yes  ☑ No
                                            Wetting yourself?          ☐ Yes  ☑ No
                                            Difficulty starting stream? ☐ Yes  ☑ No 19. Are you having any bowel problems:     Constipation?              ☐ Yes  ☑ No
                                            Diarrhea?                  ☐ Yes  ☑ No
                                            Soiling your clothes?      ☐ Yes  ☑ No

*FIG. 25*

| Pulses | | CAROTID | BRACHIAL | ABD AORTA | FEMORAL | POP | DP | PT |
|---|---|---|---|---|---|---|---|---|
| PULSES | Left | 2 | 2 |  | 2 | 2 | 2 | 2 |
|  |  |  |  | 2 |  |  |  |  |
|  | Right | 2 | 2 |  | 2 | 2 | 2 | 2 |
| BRUITS | Left | ☐ |  |  | ☐ |  |  |  |
|  |  |  |  | ☐ |  |  |  |  |
|  | Right | ☐ |  |  | ☐ |  |  |  |
| DOPPLER SIGNAL | Left | ✓ | ✓ |  | ✓ | ✓ | ✓ | ✓ |
|  | Right | ✓ | ✓ |  | ✓ | ✓ | ✓ | ✓ |

✓ normal    ⬇ reduced    o absent

Formal Lower Extremity Evaluation Performed    ☐ Yes  ☐ No   Date 5/1/96

*FIG. 26*

| Biothesiometry | | | | | | |
|---|---|---|---|---|---|---|
| | Age | Right 1st Digit | Left 1st Digit | Right Shaft | Left Shaft | Glans |
| Normal Values | 17-29 | 5 | 5 | 5 | 5 | 6 |
| | 30-39 | 5 | 5 | 6 | 6 | 7 |
| | 40-49 | 5 | 5 | 6 | 6 | 7 |
| | 50-59 | 6 | 6 | 8 | 8 | 9 |
| | 60-69 | 6 | 6 | 9 | 9 | 10 |
| | 70-80 | 7 | 7 | 14 | 14 | 16 |
| Normal Values | | 5 | 5 | 6 | 6 | 7 |
| Measured Values 38 YRS | | 4 | 4 | 4 | 4 | 4 |
| Normal/Abnormal (N/ABN) | | NORMAL | NORMAL | NORMAL | NORMAL | NORMAL |

*FIG. 28*

RigiScan

|  | Session 1 | Session 2 | Normal Values |
|---|---|---|---|
| Date | 5/28/96 | 5/29/96 | |
| Duration in hours | 8 | 8 | |
| Number of events | 5 | 5 | 3-6/8 Hrs |
| Resting Tumescence (cm) | 2 | 2 | |
| Max Tumescence Increase | | | |
| − Tip (cm) | 2 | 2 | 2 cm |
| − Base (cm) | 3 | 3 | 3 cm |
| Max Duration (min) | 30 | 30 | > 30 min |
| Average Duration (min) | 20 | 20 | > 20 min |
| Max Rigidity (%) | 70 | 70 | 70% |
| Dissociation (% of Events) | 50 | 50 | < 50% |
| Uncoupling (% of events) | 50 | 50 | < 50% |
| Plots Attached | ☑ Yes ☐ No | | |

Serum Evaluation

Measured only by specific request of physician

|  |  | Normal Range |
|---|---|---|
| Glucose (Fasting) (mg/dl) | 84 | 62-128 |
| TST (ng/dl) | 400 | 300-1000 |
| Prolactin (ng/ml) | 19.7 | > 18.5 |
| LH (mIU/ml) | 13.8 | < 25.0 |
| Lab: | Ace Clinical Lab. (5/1/96) | |
| Office: | | |
| Other: | | |

*FIG. 29*

Venous Evaluation — Lower Extremities

Patient Information

Name: Ni, Michael J    Date: 5/30/96
SSN/ID: 590-    Sex: M    Age: 38    Date of Prior Evaluation: New
Referring Physician: Reese    Examined By: BK

History and Physical Findings

|  | Trauma | Edema | Calf Tenderness | Skin Changes | Varicose Veins | Previous DVT |
|---|---|---|---|---|---|---|
| Left | Y-1 | N | Y-2 | N | N | N |
| Right | N | N | N | N | N | N |

Pleural Discomfort: N    Hormone Use: N    Hypercoagulability: N    Malignant Disease: N CVA: N    CHF: N    Other: N S/P and Notes:
1 – Localized trauma to the left ankle three months ago
2 – Tenderness for approximately three months during exercise following trauma

*FIG. 31*

VENOUS EVALUATION POINTS

| R | | L |
|---|---|---|
| 3.4 | From MVO Curve | 3.4 |
| 0.00 | From SVC Ratio (min/max) Curve | 0.00 |
| 0 | Absent Venous Respiratory Waves [2] | 0 |

Abnormal Venous Doppler Signals

| R | | L |
|---|---|---|
| 0 | Femoral [1] | 0 |
| 0 | Popliteal [1] | 0 |
| 0 | Post Tibial [1] | 0 |
| 3.4 | TOTAL SCORE | 3.4 |

FIG. 34

Arterial Evaluation – Lower Extremities

Patient Information

Name: Ba, David B  Date: 5/30/96
SSN/ID: 400-  Sex: M  Age: 33  Date of Prior Evaluation: New
Referring Physician: Jefferson  Examined By: B K

Vascular History

| | | | | | | | |
|---|---|---|---|---|---|---|---|
| Cigarette Smoking | Current-1 | Hypertension | N | Diabetic | No | MI | N |
| Hyperlipidemia | N | Obesity | N | Claudication | N | Angina | N |
| Headache | N | Dysphasia | N | Syncope | N | Vertigo | N |
| Amaurosis Fugax | N | Hemiplegia | N | Dizziness | N | | |
| Asymptomatic | N | TIA | N | CVA | N | | |

S/P and Notes

1 - Twenty-Five Pack Year History
2 - Current Medication (10 Years)
3 - Single episode of Left AF of 5 minute duration with complete recovery. Occurred 3 days ago.

Brachial Blood Pressure: 160 / 90   Arm: (L)eft/(R)ight  R

Arterial Pulse

| Pulses | | 0 | Reduced | Normal | Bruits by Auscultation |
|---|---|---|---|---|---|
| Carotid | Left | ☐ | ☐ | ☑ | ☑ |
|  | Right | ☐ | ☐ | ☑ | ☐ |
| Temporal | Left | ☐ | ☐ | ☑ | ☐ |
|  | Right | ☐ | ☐ | ☑ | ☐ |
| Facial | Left | ☐ | ☐ | ☑ | ☐ |
|  | Right | ☐ | ☐ | ☑ | ☐ |

*FIG. 36*

Carotid Evaluation

WARNING
If any Contraindication is selected, the OPG test will not be performed.

OPG Contraindications ☑ None

When a patient presents with any of the following situations, OPG pressures are not recommended:

☐ Untreated or Unstable Glaucoma

☐ Acute or Chronic Conjunctivitis

☐ Hx or Spontaneous Retinal Detachment or Recent Eye Trauma

☐ Allergy to Topical Anesthetic or the Eye Cup Material (Lucite)

Side Effects of OPG Testing

Subconjunctival Edema*
Subconjunctival Ecchymosis*
Mild Ocular Abrasion

\* These side effects are minimal and clear rapidly without treatment.

---

Ocular Pneumoplethysmography (OPG)

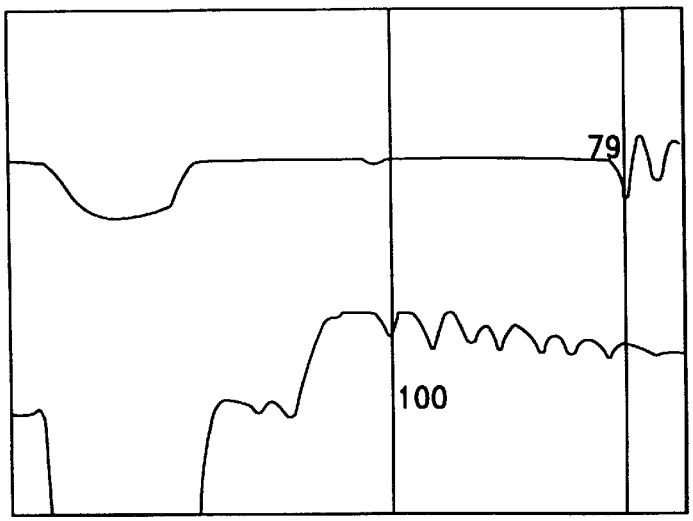

Ophthalmic Artery Pressure (mmHg)   Left  79
                                     Right 79

*FIG. 37*

Carotid Evaluation

Carotid Audiofrequency Analysis (CAA)

Cardiac Murmur ☐ Yes ☑ No      Subclavian Bruit ☐ Yes ☑ No

Left

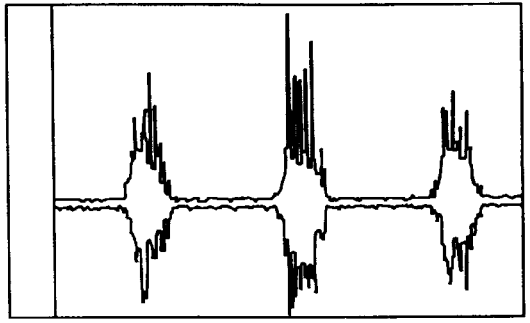

- ☐ Normal
- ☐ Fully/Partially Transmitted
- ☐ Increased Frequency < 1/2 Systole
- ☑ Increased Frequency > 1/2 Systole
- ☐ Increased Frequency Diastole Right

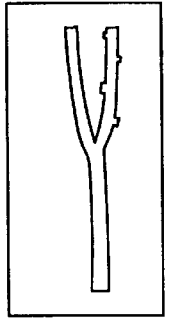

- ☑ Normal
- ☐ Fully/Partially Transmitted
- ☐ Increased Frequency < 1/2 Systole
- ☐ Increased Frequency > 1/2 Systole
- ☐ Increased Frequency Diastole

Continuous Wave Doppler Exam

| Doppler Signals | | | 0 | Reduced | Forward | Reversed |
|---|---|---|---|---|---|---|
| Supraorbital W Temporal Compression | | Left | ☐ | ☐ | ☐ | ☑ |
| | | Right | ☐ | ☐ | ☑ | ☐ |
| | | Left | ☑ | ☐ | ☐ | ☐ |
| | | Right | ☐ | ☐ | ☑ | ☐ |
| W Facial Compression | | Left | ☐ | ☐ | ☑ | ☐ |
| | | Right | ☐ | ☐ | ☑ | ☐ |
| Extracranial Vertebral | Proximal | Left | ☐ | ☐ | ☑ | ☐ |
| | | Right | ☐ | ☐ | ☑ | ☐ |
| | Distal | Left | ☐ | ☐ | ☑ | ☐ |
| | | Right | ☐ | ☐ | ☑ | ☐ |

FIG. 38

INTEGRATED, PERIPHERAL VASCULAR DIAGNOSTIC SYSTEM AND METHOD THEREFOR

This is a continuation of U.S. patent application Ser. No. 08/968,910 filed Nov. 6, 1997, which is now U.S. Pat. No. 6,017,307, which was a continuation of Ser. No. 08/662,438, filed Jun. 10, 1996, now abandoned, which was a regular patent application based upon provisional patent application Ser. No. 60/018,784 filed May 31, 1996.

This is a regular patent application based upon provisional patent application, Serial No. 60/018,784, filed May 31, 1996.

The present invention relates to an integrated, peripheral vascular diagnostic system which electronically links several vascular diagnostic medical equipment, and a method therefor.

BACKGROUND OF THE INVENTION

In general terms, if a patient presents initially with peripheral vascular disease, there is about a 90% chance that the patient also has coronary artery disease. On the other hand, if the patient initially presents with coronary artery disease, 10% of those patients have some evidence of peripheral vascular disease. In general, coronary artery disease generally presents itself in a patient earlier in life than does peripheral vascular disease, and both are manifestations of the atherosclerotic process.

Over the last decade, there has been a steady decline in cardiac morbidity and mortality. This is due to many reasons, including better risk factor control (reduction in smoking), the availability of anti-arrhythmic drugs, beta blocking drugs, calcium channel blocking drugs, and coronary bypass surgery. During this same period of time, there has been no tremendous scientific breakthroughs in the generalized atherosclerotic process.

As a result of the foregoing factors, there is a reasonable segment of the population who would have died of coronary artery disease, but now those patients live to present with peripheral vascular disease. In addition, over the past decade, there has been a sizeable increase in the number of people over 55 years of age and those people are generally classified as being "at risk" for peripheral vascular disease.

A wide range of physicians may deal with some type of vascular analysis. For example, general and family medicine physicians may study extremity symptoms and cerebral symptoms; cardiologists may study extremity systems, cerebral systems, and determine the degree of atherosclerosis; vascular surgeons are involved in extremity reconstruction, extra-cranial arterial disease and others; neurologists are involved in the study of cerebrovascular disease; radiologists are involved in interventions such as angioplasty, planing, and handling complications; orthopedics are involved in amputation healing and post-operative deep venous thrombosis (DVT); dermatologists are concerned about lesion healing; podiatrists are concerned about lesion healing and clearance for foot surgery; urologists are involved in the study of male impotence; obstetricians are involved in the study of deep venous thrombosis (DVT) and ophthalmologists study retinal emboli.

The most common evaluations in a vascular lab fall into three categories. First, there is evaluation of the arteries that supply blood to the lower body extremities of the patient. When an occlusion occurs in this area, the symptoms may range from resting foot pain, to the development of ulcers due to lack of blood flow, to pain only when walking. Further, vascular laboratories are sometimes requested to determine the presence or absence of thrombosis of the deep venous system in the lower extremities. Thirdly, these vascular laboratory facilities evaluate the degree of carotid artery disease. The carotid artery supplies the brain with blood and, when diseased, is a major cause of cerebrovascular accidents (i.e., stroke). Miscellaneous studies at vascular laboratories involve the study of upper extremities, compression syndromes, and male impotency (MI) studies.

Currently, there are pulse volume recorders available to study the upper and lower extremities of a patient. Such a study correlates the amount of blood flowing beneath a pressure cuff with each heartbeat of the patient. Bi-directional continuous wave ultrasound doppler probes are utilized to detect the movement and direction of blood flow through arteries and veins. Audio-frequency analyzer (AA) units are utilized by technicians and physicians to listen to and characterize the blood flow via a sensitive microphone. This involves an analysis of the audio signals. Ocular pneumoplethysmographs (OPG) are utilized to measure the ophthalmic artery pressure in the eyes of a patient. Photoplethysmographs (PPG) are used to monitor blood flow for histolic pressure measurements, venous reflux testing, and arterial blood flow. One example of bi-directional continuous wave ultrasound doppler system is manufactured by Hokanson as Model MD6. An OPG is manufactured by Electro-Diagnostic Instruments (EDI) as Model OPG-5D. AN PPG is manufactured by Hokanson, Model MD6RP.

In the past, all these instruments have been used independently to study the vascular system of a patient.

OBJECTS OF THE INVENTION

It is an object of the present invention to provide an integrated peripheral vascular diagnostic system and a method therefor.

It is a further object of the present invention to provide an integrated vascular diagnostic system which electronically links several non-invasive vascular diagnostic equipment such as a pulse volume recorder or PVR, an ocular pneumoplethysmograph (OPG), a photoplethysomograph (PPG), an audio-frequency analysis (AA) unit and/or a doppler ultrasound unit.

It is an additional object of the present invention to accept electronic data signals from one or more of these instruments, to compile the information into a database and to generate reports which provide an analysis of the vascular information collected from the patient as well as analog representations of the digital data corresponding to the instrument data obtained from the medical instruments.

It is a further object of the present invention to provide a playback unit such that the technician analyzing and compiling the vascular diagnostic report can, simultaneous with the preparation of the electronic vascular report, listen to analog representations of the ultrasound doppler and the audio-frequency AA analysis signals.

It is an additional object of the present invention to be able to combine the keypad entry data with the instrument data in the database and transmit that information to other computer systems for further study and analysis of the vascular data.

It is another object of the present invention to provide a method for integrating a vascular diagnostic system with those non-invasive vascular medical devices.

SUMMARY OF THE INVENTION

The integrated peripheral vascular diagnostic system electronically links a pulse volume recorder PVR, an ocular pneumoplethysmograph OPG, a photoplethysmograph PPG, an audio-frequency analyzer AA unit which characterizes blood flow with a sensitive microphone, and a doppler ultrasound unit. This diagnostic equipment generates data signals. These data signals are converted into digital data signals and are stored in a database. The diagnostic system includes a computer with a processor, a memory, a keypad input device, a display monitor, a printer and an interface for connecting these electronic components together along with an interface for the PVR, OPG, PPG, AA and doppler ultrasound. The diagnostic system further includes a report generator which generates, displays and prints a plurality of vascular diagnostic reports from the digital instrument data signals and the keypad entry data. The diagnostic system also includes, in a further embodiment, an audio playback device such that the technician, when preparing the vascular diagnostic report, can listen to analog versions of the digital instrument data signals. The method for electronically integrating the vascular diagnostic system includes electronically obtaining and converting the instrument data signals into digital data signals, inputting keypad entry data representing manually acquired vascular medical data from the patient, compiling the digital data and the keypad entry data into a database and generating, displaying and printing a plurality of vascular diagnostic reports.

BRIEF DESCRIPTION OF THE DRAWINGS

Further objects and advantages of the present invention can be found in the detailed description of the preferred embodiments when taken in conjunction with the accompanying drawings in which:

FIGS. 15–39 illustrate exemplary vascular diagnostic reports prepared by the report generator as part of the diagnostic system.

DETAILED DESCRIPTION OF THE PREFERRED EMBODIMENTS

The present invention relates to an integrated peripheral vascular diagnostic system and a method therefor.

Figure 1:
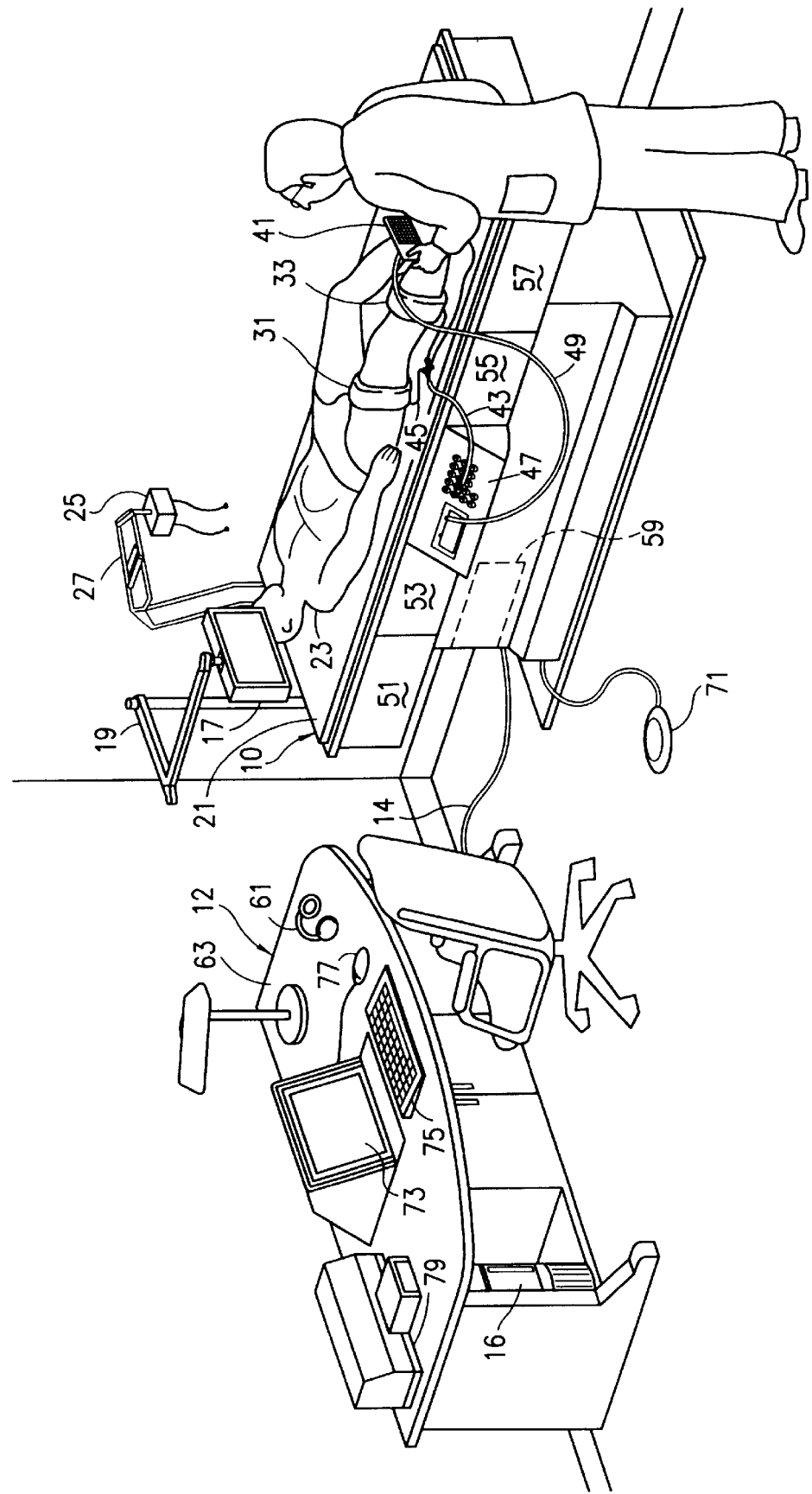
FIG. 1 diagrammatically illustrates one embodiment of the integrated peripheral vascular diagnostic system which includes an examination unit (EU) and an analyzing unit (AU)

FIG. 1 diagrammatically illustrates the vascular diagnostic system as including an examination unit 10 and an analyzing unit 12. Both units include computer systems and these computer systems are electronically linked together via cable 14. A local area network or LAN permits the electronic communication and sharing of information between the computer 16 in analyzing unit 12 and the computer installed internally within the examination unit 10.

Examination unit 10 includes a flat screen monitor 17 which is hung on movable support pole and arm system 19 above table surface 21. During the vascular examination, the technician is prompted to conduct certain vascular tests or examinations based upon instructions presented on flying display monitor 17. Since display monitor 17 can be moved in the x, y and z directions due to the rotational, transverse and translation of supporting arm system 19, flying monitor 17 can be moved out of the way of patient 23.

One type of vascular examination involves the use of an ocular pneumoplethysmograph OPG 25. OPG 25 is also suspended above examination table surface 21 on supporting arm system 27. OPG 25 can be rotated, translated and moved transversely away from examination table top 21.

In order to conduct several vascular examinations on patient 23, the technician snugly places one or more pressure cuffs 31, 33 on the legs or arms of patient 23. The technician initiates, with the proper controls on remote control device 41, a sequential increase of pressure in cuffs 31, 33. Pressure sensors in the closed pneumatic system sense the flow of blood in the patient's vascular system. This is commonly identified with the use of pulse volume recorders or PVRs. In order to pump up and sense the change in blood flow via the change in pressure in the closed pneumatic system, pressure cuffs 31, 33 are pneumatically linked to a pump and pressure sensor via combination umbilical pressure tube 43 which carries individual pressure tubes, one of which is pressure tube 45. These pressure tubes are pneumatically coupled to a test port panel 47. Remote control device 41 is electrically connected via electrical cable 49 to the test port panel 47 through an aperture in the panel.

Examination unit 10 includes a number of pull-out drawers or piano hinge front panels 51, 53, 55, and 57 as well as a pull-out drawer 59. In each one of these drawers, the technician can store various pressure cuffs, cables, and other connective devices or medical supplies which may be used during the vascular examination of patient 23. Additionally, disposed in the interior of one or more of these drawers is the pulse volume recorder PVR, the ophthoplethysmograph, equipment for the audio-frequency analysis AA unit and particularly the sensitive microphone used in connection with that unit, and the continuous wave doppler ultrasound unit as well as the doppler probe. Test port panel 47 (discussed later in connection with FIG. 3), provides both a pneumatic and electrical connection port to the pressure cuffs, pressure cuff tubes (43, 45) and electrical ports for the connection to the electrical sensing devices such as the sensitive microphone for the AA unit and the ultrasound probe for the doppler ultrasound unit.

As is common in vascular tests, the technician may wear a pair of microphones 61 which are placed on table top 63 of analyzing unit 12. Particularly, when using the doppler ultrasound, the technician will wear headphone 61 about his ears and blood flow in one direction is identified by an audio sound in one ear as compared with blood flow in the opposite direction which is identified by an audio sound in the other ear. Headphones 61 are cordless headphones and as such they receive a radio frequency RF signal transmitted by the computer system in the examination unit. Remote control device 41 enables the technician to walk around and move about patient 23 while patient rests on table top 21 of examination unit 10. Further, flying monitor 17 enables the technician to move and adjust the monitor for the best view during the vascular examination.

Examination unit 10 also includes a foot control 71.

Additionally, examination unit 10 may include an external speaker if the technician wants to audibly hear the ultrasound signals or the audio frequency signals.

Analyzing unit 12 includes a computer system 16, a monitor 73, a keyboard 75, a mouse or track ball 77, and a printer 79 which is preferably a color printer. All of these electrical equipment are connected together as is common in the industry. In addition, there is a computer system in examination unit 10 which is not immediately identified in FIG. 1. The computer system in examination unit 10 is electrically connected via cabling 14 and a local area network (Ethernet) to computer system 16.

During the report generation phase, the technician can wear headphone 61 and view the vascular reports on display monitor 73. By inputting the proper command controls via mouse 77 or keyboard 75, the user can listen to the analog version of the stored digital instrument data signals. In this manner, the technician can associate in the electronic format the audio doppler signals and the audio-frequency analysis AA signals while he or she prepares the vascular diagnostic report for the particular patient. Since the digital instrument data signals are electronically linked in the database to the keypad entry data signals, a complete vascular diagnostic report can be visually presented on monitor 73 to the technician and also audibly presented to the technician. Since this data is electronically connected together, the data as well as the report can be sent over a wide area network or over the Internet to other computer systems for further analysis and review by other physicians.

As used herein, the term "digital instrument data signals" refers to the digital version of any instrument data signals output by the vascular medical equipment, e.g., the PVR, OPG, doppler or OPP.

One of the important features of the present invention is the integrated nature of the entire vascular diagnostic system. This system prompts the technician to conduct the vascular exams in a certain manner, request keypad entry data from the technician, prompts the technician to gather certain instrument data signals such as signals from the PVR, OPG, PPG and AA as well as the ultrasound doppler signals, places all this data in a database, and then enables the technician to generate a vascular diagnostic report.

The AU or analyzing unit provides a means to gather and store all necessary data about a patient in order to characterize his vascular health. Certain data will be provided by external input. The system operator or technician will either input data using a keyboard (keyboard entry data) or reload data from an auxiliary storage tape. Current vascular data will be generated and stored based on running a series of diagnostic exams on the patient by the operator at the EU or examination unit.

The AU also provides a means to input and store all appropriate census, vascular history, vascular studies required, and other patient data from an external source. New information will be entered via keyboard. Previously gathered information stored on an auxiliary storage tape will be reinstalled on the system. This enables the technician to compare current vascular exam data with previously obtained data. Any patient data currently in the system will be augmented or updated via the keyboard.

The AU will take the vascular study requirements data and translate it into the specific diagnostic tests needed to be performed at the EU.

The EU enables the technician to gather patient vascular data. It provides a means to gather and store all necessary vascular data by running a series of diagnostic tests on the patient. The diagnostic tests to be run are as defined by the AU and the selected tests are either downloaded to the computer system in the EU or commands representing the selected tests are sent via the Ethernet LAN to the EU computer system. Diagnostic tests are run using the following instruments in the EU examining table:

Pulse Volume Recorder (PVR)—The function of the PVR is to obtain a series of waveforms from a set of cuffs on either the lower or upper extremities which correlates to the amount of blood flowing beneath it with each heartbeat. Also segmental systolic pressures can be measured using the occlusion technique.

Bi-directional Continuous-Wave Doppler—The function of the ultrasound doppler is to detect movement and the direction of blood flow in both arteries and veins. The probe sends and receives ultrasound waves. The changes in frequency of the emitted and received signals are processed electronically and presented as either a sound in the headphones 16 and/or as a waveform on the display 17.

Audiofrequency Analyzer (AA)—The function of the AA is to listen and characterize blood flow via audio means using a sensitive microphone. The received signals are processed electronically and presented as either a sound in the headphones 16 and/or as a waveform on the display 17.

Ocular Pneumoplethysmograph (OPG)—The function of the OPG is to measure ophthalmic artery pressure in both eyes. Small suction cups are placed on the sclera of the eyes. These eyecups record minute volume changes during a continuously declining vacuum. This vascular exam has been correlated with the intraocular pressure. The intraocular pressure at the time of the first ocular pulsation is stored as the ophthalmic systolic pressure. The received instrument data signals are processed electronically and presented as a waveform on the display 17.

Photoplethysmograph (PPG)—The function of the PPG is to monitor blood flow for systolic pressure measurement, venous reflux testing, and arterial blood flow. The PPG probe emits a measured amount of light from a light emitting diode (LED) into the tissue and measures the amount of light returned to the probe. The difference between the two measurements is actually the quantity of blood in the tissue. The blood actually absorbs some of the light from the LED.

The received signals are processed electronically and presented as a waveform on the display 17.

Computer Hardware Subsystem

EU or examination unit gathers and stores all necessary vascular data based on running a series of diagnostic tests or exams on the patient by the operator. The EU consists of the examining table, diagnostic modules, a computer subsystem, and a step stool.

The examining table houses the diagnostic modules and the computer subsystem. It provides a place for the operator to gather data from a reclining patient using the diagnostic modules. In one embodiment, the examining table is made of wood with all exterior surfaces covered in formica. The total table height (to top of the comfort pad) is 32 inches. It is topped with a two-inch thick comfort pad. Fixtures located on the side of the table at its head allow the OPG eye cup transducer support arm assembly, along with the monitor arm assembly 19, to be conveniently mounted. This 14-inch diagonal flat screen monitor is mounted on a swing-arm and support post above the table surface. The OPG transducer arm 27 swivels in its mount. There are two pull out arm rest shelves located just below the top's formica surface. The OPG footswitch 71 extends from its cord at the table's base.

Figure 3:
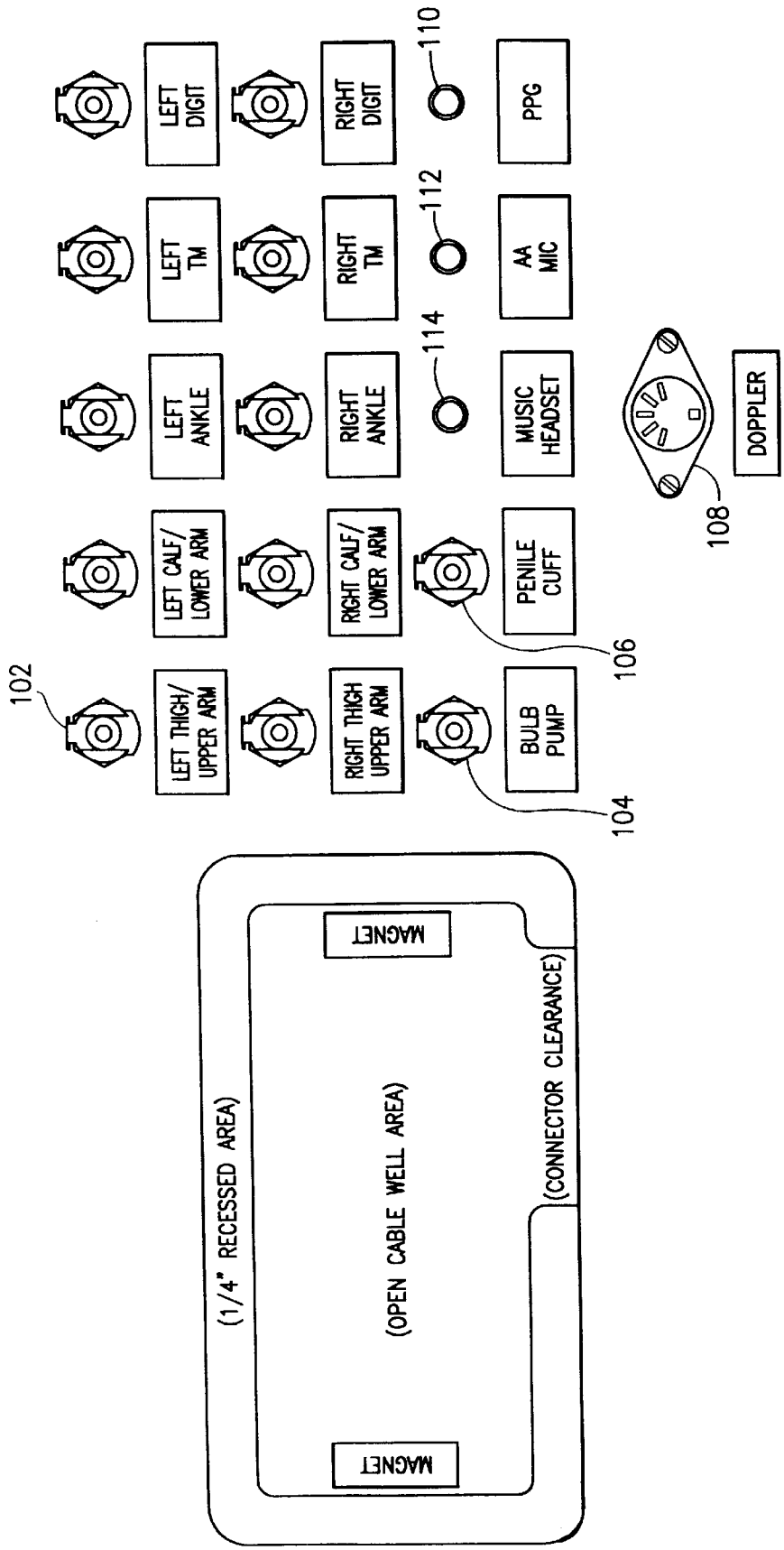
FIG. 3 diagrammatically illustrates the test port panel for pressure tubes, electrical connections and the remote control device.

FIG. 3 diagrammatically illustrates a test port panel. The table has a test port panel 47 that has quick disconnect tube fittings, one of which is fitting 102, for the cuffs. See FIG. 3. An additional quick disconnect is provided for a hand pump bulb/valve assembly 104 and penile cuff fitting 106. There are four electrical jacks for the doppler electrical data and control port 108, PPG electrical port 110, microphone port 112, and patient music headset port 114. Each connection port and control port has its own identifying label plate. The test port panel is tilted out to 45 degrees during use so that it can readily be seen by the operator to make connections and manipulate controls.

There are 11 air tubing quick disconnect ports for cuffs. This includes the following:

Pneumatic Quick Disconnect Ports

Right Leg/Upper Arm Cuff

Left Leg/Upper Arm Cuff

Right Calf/Lower Arm Cuff

Left Calf/Lower Arm Cuff

Right Ankle Cuff

Left Ankle Cuff

Right TM Cuff

Left TM Cuff

Right Toe Cuff

Left Toe Cuff

Penile Cuff

There are at least three electrical jacks in the test port panel. The fourth jack 114 for a music headphone connection for patient listening necessitates the addition of a small portable audio CD player in the examination table. The electric jacks are listed below:

Electrical Port Table

Doppler Probe

PPG

Audiofrequency Analyzer Microphone

Patient Music Headphone (option)

Figure 2:
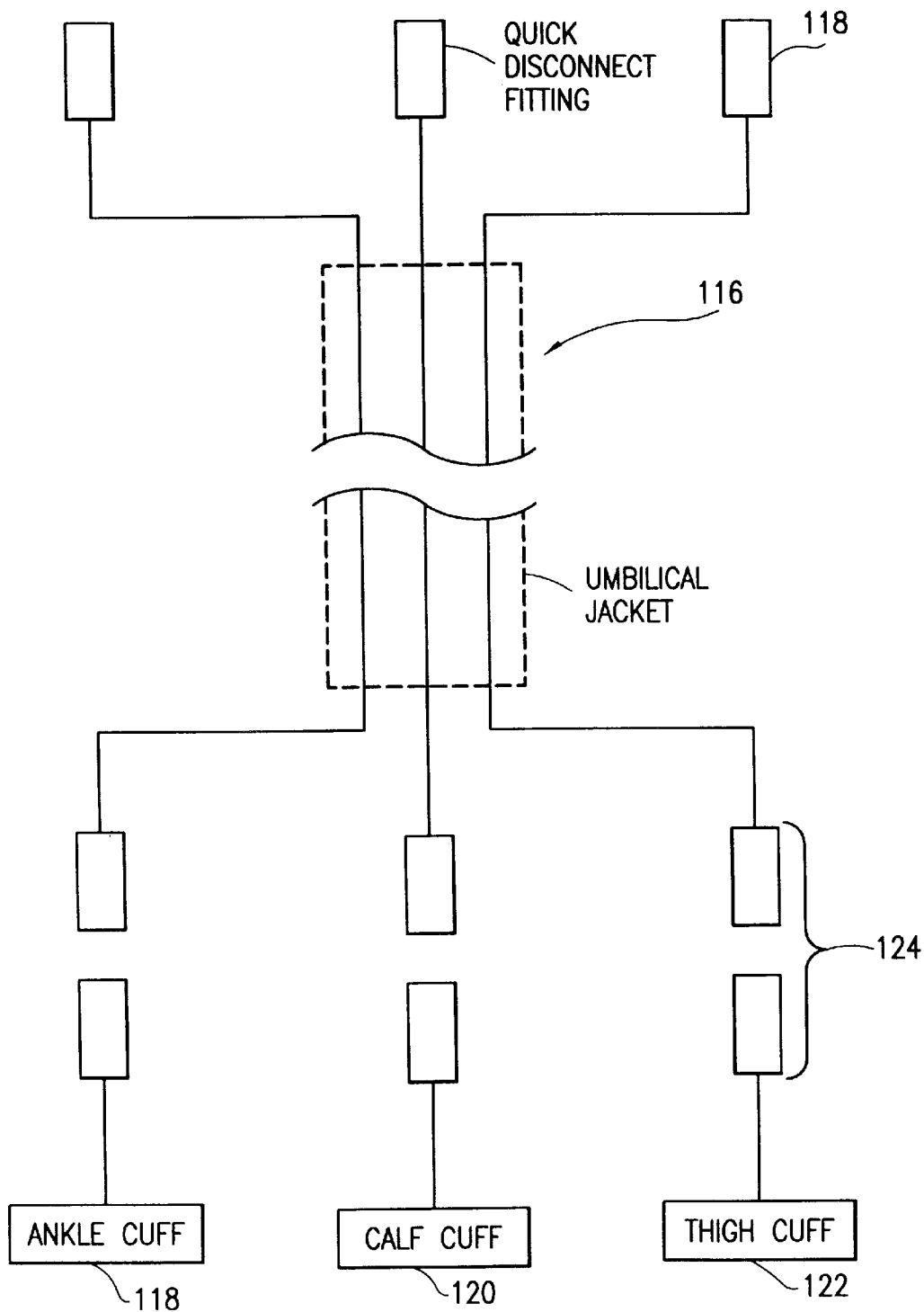
FIG. 2 diagrammatically illustrates a cuff tube umbilical unit which provides quick connection between the pressure tube ports and the cuffs placed on the patient during a vascular study.

FIG. 2 diagrammatically shows combination or umbilical cord 116 for pneumatically linking ankle, calf and thigh cuffs 118, 120, 122 to the pneumatic system in the examination unit EU 10. These cuffs have quick disconnect couplers, one of which is coupler set 124 which connects to umbilical cord set 116. The opposite end has quick disconnect fittings 118 which pneumatically connect with the ports on test port panel 47. See pneumatic port 102. The umbilical cord set permits the operator/technician to better organize multiple pressure tubes during a PVR exam.

The test port panel diagrammatically illustrated in FIG. 3 holds a Remote Control Device (RCD) (diagrammatically illustrated in FIG. 5) that is used in place by the operator or is removed for use on a hand-held basis. The RCD is held in place on the panel with magnetic catches. The RCD is used by the operator to control the diagnostic tests. During patient audiofrequency amplifier (AA) testing the operator uses wireless headphones 61 during the course of the tests. An AA microphone is plugged into the test port panel at electrical port 112.

The configuration of the examination table consists of a top section and a recessed base section. The top section has a table top surface, pad, slide-out arm rests, test port panel, computer storage area and three drawers. There will be sufficient storage for most of the diagnostic instruments, CPU assembly, cuffs, and probes. There will also be some storage space for medical supplies such as linen sheets, towels and latex gloves. The test port panel is located on the middle of the side panel between two sets of two drawers. The left most drawer near the monitor swingarm 19 is a false drawer. It has a bottom hinged front with a touch latch at the top to allow access to the CPU assembly housed behind it. The other drawers are accessed by recessed grip surfaces running along the bottom of the drawers. The recessed base section has a pedestal. The pedestal houses the OPG and the UPS. The OPG is located in a pull-out drawer on the side of the pedestal.

Figure 4:
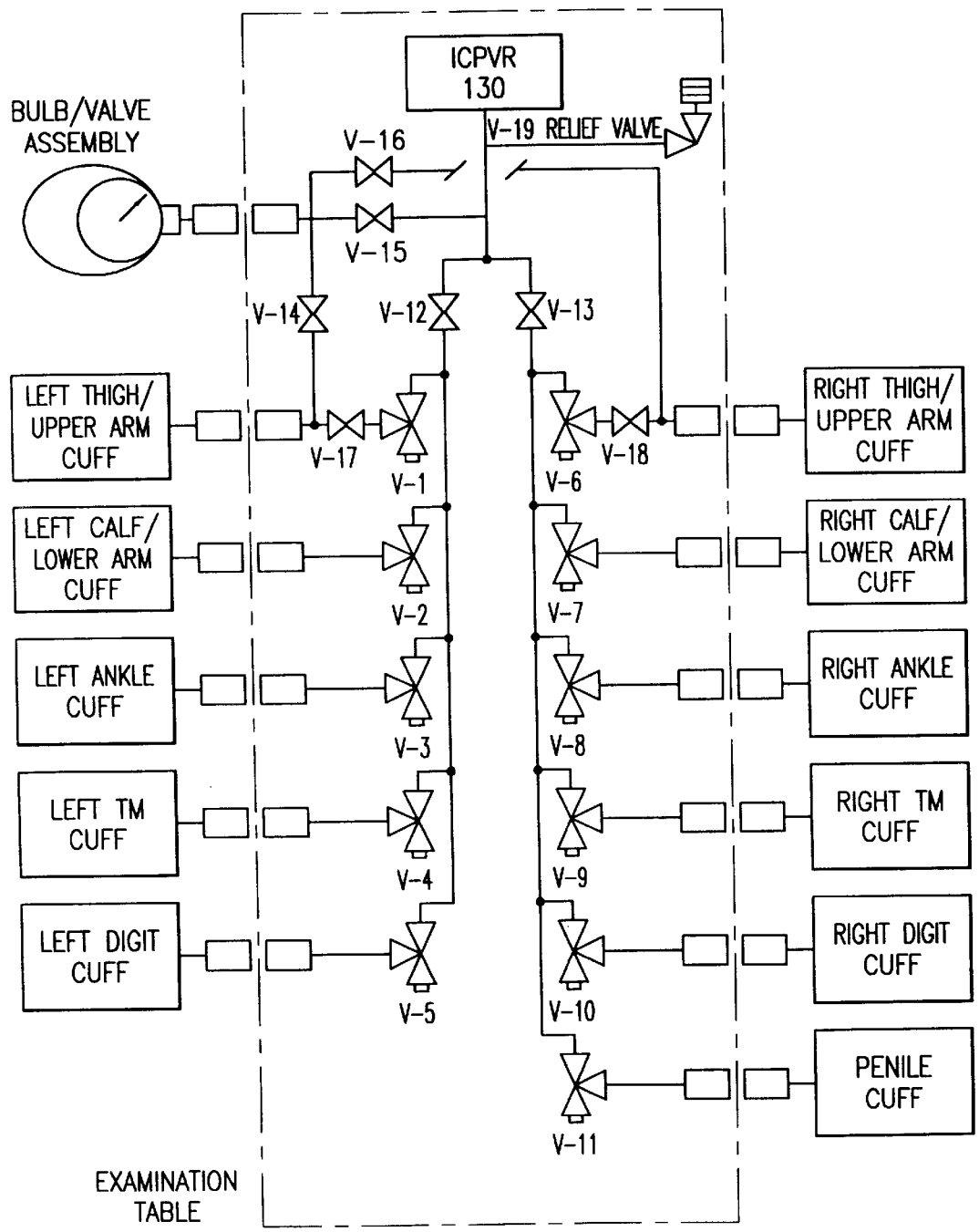
FIG. 4 diagrammatically illustrates a pneumatic schematic for the valve system for the internally calibrated PVR (ICPVR)

FIG. 4 diagrammatically illustrates the pneumatic schematic for the present invention.

As discussed earlier, one or more pressure cuffs are placed on the extremities of patient 23 during a certain vascular exams. These cuffs are commonly used in connection with a pulse volume recorder.

The internally calibrated pulse volume recorder 130 or ICPVR is a board installed in an expansion slot of the computer system located in the examination table. Flexible tubing running from the ICPVR connects to two- and three-way solenoid valves that route air pressure to the correct test port panel quick disconnect fittings.

The blood pressure cuffs for use with the current embodiment of the peripheral vascular lab or PVL are discussed below. They are sized to be used with specific locations on an adult. All cuffs are of the single tube style. The cuffs are connected to tubing that ends with a quick disconnect fitting that plugs into an appropriate port on the test port panel.

Thigh—Single tube Bladder and Cuff Assembly, Baum "Thigh" Cuff

Calf/JUpper Arm—Single tube Bladder and Cuff Assembly, Baum "Large Arm" Cuff

Lower Arm—Single tube Bladder and Cuff Assembly, Baum "Adult" Cuff

Ankle—Single tube Bladder and Cuff Assembly, Baum "Large Arm" Cuff (same cuff as for Calf)

Transmetatarsal (TM)—Single tube Bladder and Cuff Assembly, Baum "Child/Small Adult" Cuff 1st Digit—Single tube Bladder and Cuff Assembly, Hokanson Penile—Single tube Bladder and Cuff Assembly, Hokanson.

The umbilical cable assembly of FIG. 2 is made up of three tubes combined into one unit. It simplifies the leg cuff hookup process. The umbilical's tube ends have quick disconnect fittings to allow the thigh, calf and ankle cuffs to be easily connected to the test port panel.

The bladder pressurization bulb/flow control valve assembly is used to allow cuffs to be manually pressurized and deflated. This bulb assembly made by Baum will be connected to tubing that connects to the pressurization valve via a test port panel connection.

FIG. 4 shows a plurality of controllable solenoid valves. These miniature solenoid valves are used to electronically select the specific blood pressure cuffs to be pressurized by the ICPVR. The two-way valves (V-12, V-13) are used to select between the two legs/arms cuff positions while the three-way valve (e.g., V-1) is used to select a specific cuff. Additional two-way valves (V-17, V-14, V-16, V-15, V-18) are installed to support a specific test that requires the thigh cuff to be isolated and pressurized/deflated using the hand bulb while the calf cuff is being pressurized simultaneously by the ICPVR card. All of these valves are located within the examination table behind the test port panel. Relief valve V-19 is also provided.

Figure 5:
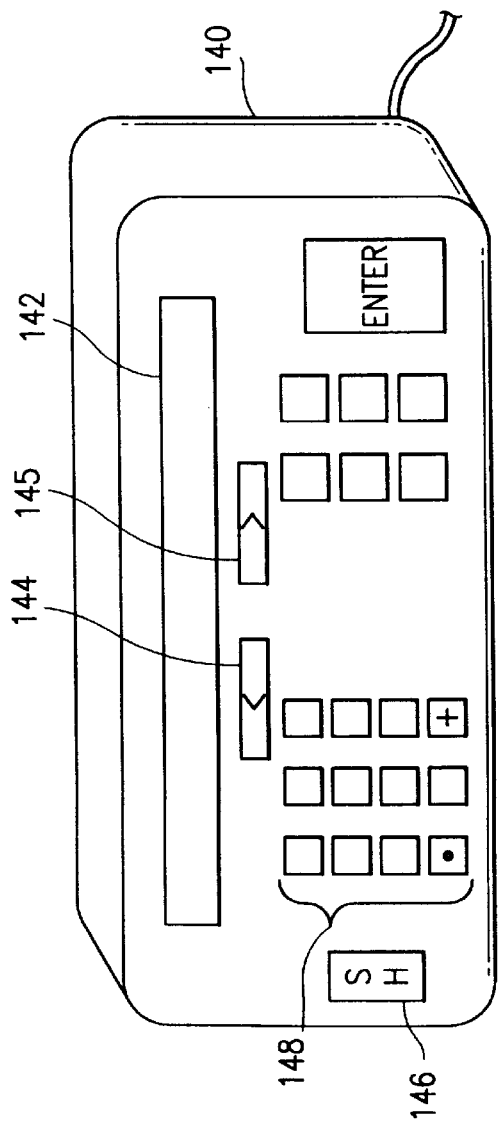
FIG. 5 diagrammatically illustrates the remote control device RCD used by the operator/technician during the vascular studies.

FIG. 5 diagrammatically illustrates remote control device RCD 140. This remote control device is utilized by the operator/technician to control the operation of ICPVR 130 and the other non-invasive medical units in this integrated system. Additionally, RCD 140 can be utilized to input keypad entry data based upon manually acquired vascular medical data from the patient.

In one embodiment, RCD 140 includes a 40 character display 142 which enables the operator to scroll through the instructions based upon the actuation of left or right arrows 144 and 145. The control device also includes a shift key 146, numerical keys 148, a period key and a plus key. The following remote control keypad table lists some of the keys that are available on RCD 140.

| Remote Control Keypad Table | |
| --- | --- |
| Left arrow | Function Key 1 - Next |
| Right arrow | F2 - End of test |
| 0–9 digits | F3 |
| Period (.) | F4 |
| Plus (+) | F5 |
| Shift | F6 - gain |
|  | Level 1, Lev - 2, Lev - 3, Lev- 1 |
| Enter | |

In general, the operator is prompted to conduct certain vascular exams on the patient based upon the flying monitor screen 17. Additionally, the operator can be prompted to input keypad entry data or to acquire digital instrument data based up the information on display 142 of RCD 140.

As an example, to change the exam, the operator would select function key 1 which is the next key. This command entry provides an indication to the computer system and the examination unit (FIG. 6) that the computer system must provide the operator with additional information for the next sequential vascular exam. At the end of the vascular exam, the operator presses the F2 "end of test" key.

RCD 140 has six programmable function keys, F1–F6. Function key F6 may be set to adjust the gain of the instrument data signal. Certain vascular tests or exams may require that the operator/technician adjust the gain on the signal displayed on flying monitor 17. As an example, programmable function key F6 can be programmed to adjust the gain to three distinct levels. To go from level 1 to level 2, the operator could press right arrow 145. Another depression of right arrow 145 shifts the gain from level 2 to level 3. A further depression of the arrow key returns the gain back to level 1. Of course, the gain could be adjusted by programming function F6 (or any other function key) to have multiple levels of gain.

Also, an analog gain control could be added to test port panel 47.

The enter key on RCD 140 is utilized by the operator to command a "record digital instrument data signal" to end such recording or to enter keypad entry data into the RCD.

Figure 6:
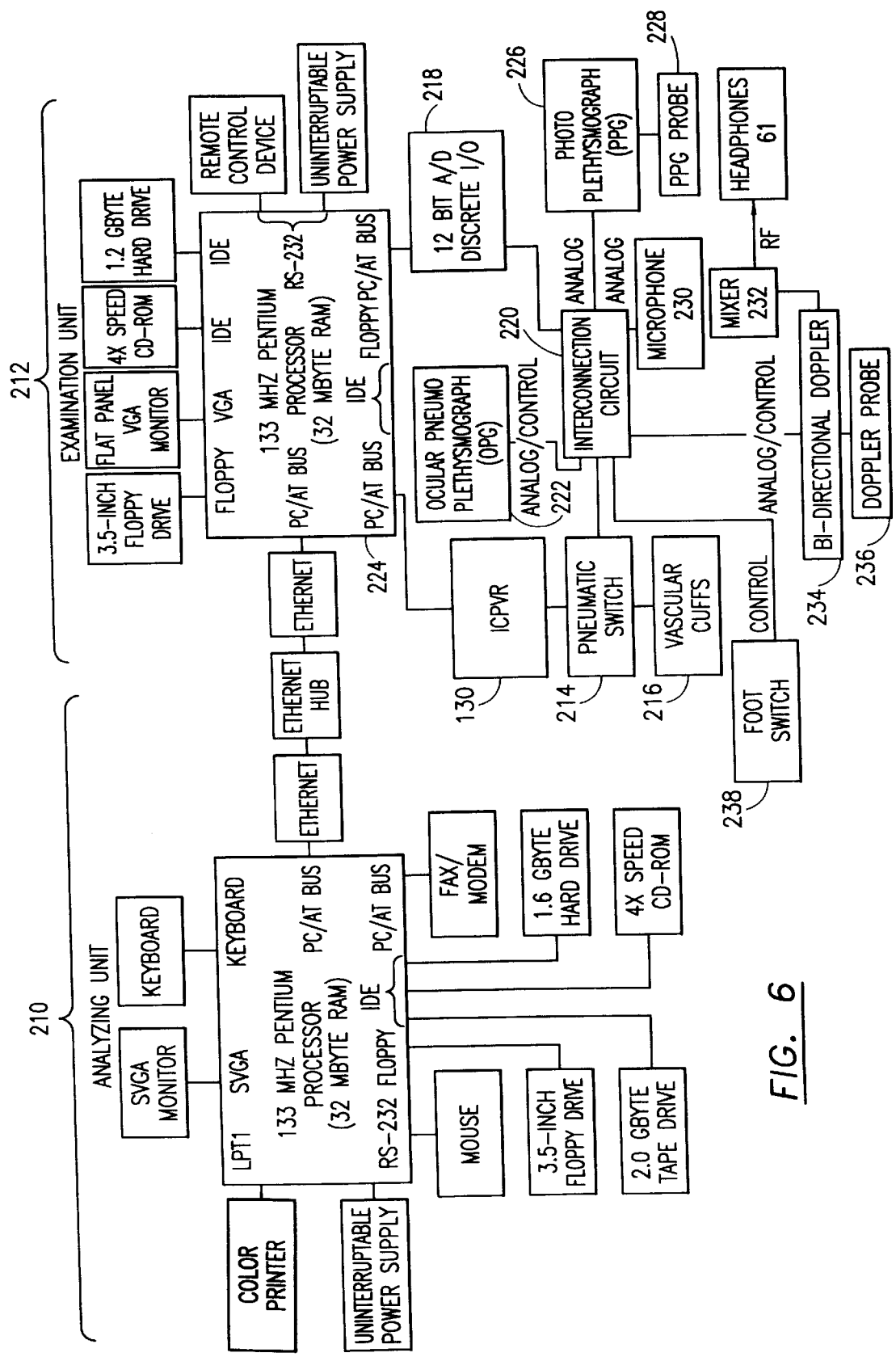
FIG. 6 diagrammatically illustrates a hardware diagram showing, among other things, electronic devices in accordance with one embodiment of the present invention.

FIG. 6 diagrammatically illustrates the electrical hardware diagram for the examination EU unit as well as the analyzing AU unit.

The computer subsystem in the AU is composed of a Pentium 133 Mhz CPU with 32 MB of RAM running Windows 95, a 1.6 GB hard drive, a 3.5-inch floppy drive, a 17-inch noninterlaced super VGA monitor, a two-button mouse, a Windows 95 keyboard, a video card with two MB VRAM, and an Ethernet interface card. Additional peripherals include a 2.0 GB internal tape backup, a 4× speed CD-ROM, a 28.8 facsimile/modem, a 600 DPI color inkjet printer, a one-KVA uninterruptable power supply (UPS), and an eight-port 10 Base T Hub for a communications interface with the EU.

The examination unit or EU 212 includes a similar type of computer system as compared with AU 210.

The Examination Unit (EU) computer subsystem provides an operator interface for control and data collection for the various vascular diagnostic instruments. The computer is a Pentium 133 MHz single board computer (SBC) with 16 MB of RAM running Windows 95, a 1.2 GB hard drive, a 3.5-inch floppy drive, a 4× speed CD-ROM, and an Ethernet interface card all contained within a slide out chassis and an AT back plane.

Display for the system will be an active matrix, thin film technology (TFT), liquid crystal display (LCD), 640×480 color VGA flat panel mounted on a swing arm above the patient and in clear view of the operator. The screen size (diagonal) is 14.2 inches with a display pitch of 0.46 mm×0.45 mm. The display weight is approximately 5.5 pounds. The display will contain a backlight and use six bits per color. The display will be powered by 5 VDC and 12 VDC from the PC chassis.

Operator control is exercised through a micro terminal remote control device (RCD), connected to the computers RS-232 interface. The unit contains a 1 by 16 by 0.25 inches high alphanumeric display with a 80 character buffer, six user-programmable keys, numeric keypad, and directional keys. The RS-232 baud rate to and from the RCD is 9600 Baud. The RCD connects to the test port panel via a cable that is long enough to allow it to be removed and used in a hand held mode.

Installed in the EU computer chassis is the ICPVR card and the analog to digital converter (ADC)/discrete input/output card. Both cards plug into the AT back plane. The ADC card digitizes analog data to 12 bits at a 100 KHz rate and stores it on the computer's hard drive for analysis and report generation. Sixteen (16) single ended inputs are internally multiplexed and are available to the ADC with a full scale input of +/−10 V and selectable gains from 0.5 to 100. The ADC card performs the function of a strip chart recorder: recording tests results for later analysis. Vascular diagnostic instruments are connected to the ADC for the recording of test results.

The discrete inputs and outputs of the ADC card are used to control the pneumatic switching for the ICPVR, PPG and Doppler operation. The foot switch for the OPG is sensed by discrete inputs to start data collection. A total of eight TTL compatible signals configurable as inputs or outputs are available for use. In order to drive the pneumatic selector valving for the ICPVR, a driver circuit is used to operate the valve's solenoids.

Examination unit 212 includes an internally calibrated pulse volume recorder ICPVR 130 which is described in detail in connection with FIGS. 8A, 8B and 8C. That ICPVR board is mounted in the computer system for EU 212. The board includes both pneumatic and electrical devices. The pneumatic output from ICPVR 130 is applied to a pneumatic switch system 214. FIG. 4 diagrammatically illustrates the pneumatic schematic of pneumatic switch system 214. The pneumatic output of pneumatic switch system 214 is fed to vascular cuffs 216. These cuffs are discussed above.

Also connected to the computer system of EU 212 is a 12 bit analog/digital and discrete input/output board 218. That board is electrically connected to an interconnection circuit 220. Further details regarding the interconnection circuit 220 is discussed later in connection with FIG. 7. Analog and control information is applied from interconnection circuit 220 to the OPG 222. Accordingly, control signals are applied to OPG 222 from interconnection circuit 220 and analog instrument data signals are generated by OPG 222 and supplied to interconnection circuit 220. Interconnection circuit 220 then supplies these received analog instrument data signals to the A/D input/output device 218 and device 218 converts them to digital instrument data signals. These digital instrument data signals are then processed as discussed later by processor 224 in the EU computer system 212.

Interconnection circuit 220 is electrically connected to PPG 226. PPG 226 is connected to the PPG probe 228.

Interconnection circuit 220 is also connected to microphone 230 and analog signals pass between microphone 230 and interconnection circuit 220.

Interconnection circuit 220 is also electrically connected to a mixer 232. Mixer 232 includes a radio frequency RF transmitter which sends RF signals to headphones 61. Headphones 61 include an RF receiver such that the operator can walk around the patient and listen to analog versions of the instrument data signals.

Interconnection circuit 220 is also connected to the bidirectional continuous wave doppler 234. Doppler unit 234 is electrically connected to doppler probe 236.

Interconnection circuit 220 is also connected to foot switch control 238. As discussed herein, foot control 238 is used in connection with OPG 222.

Figure 7:
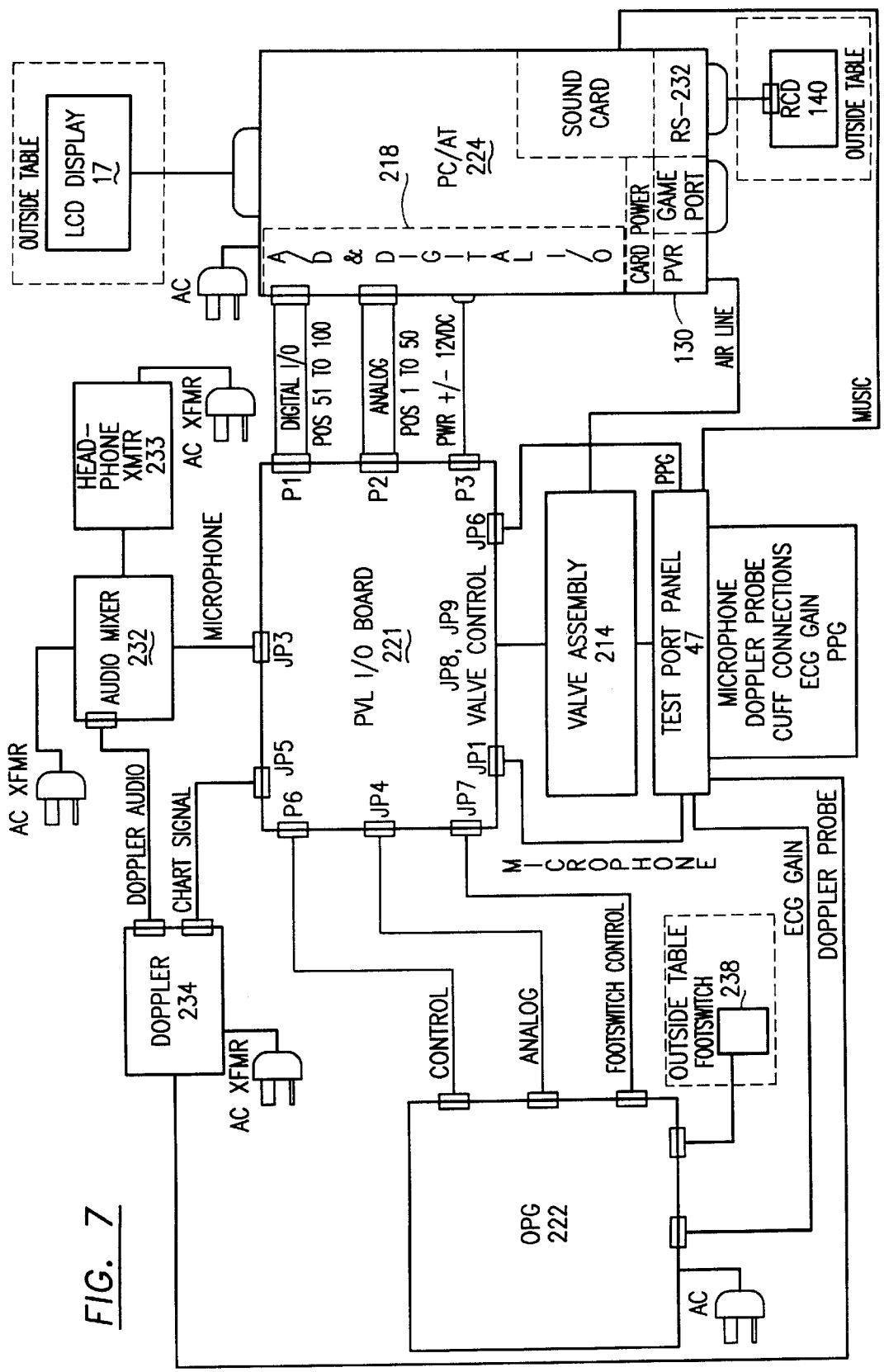
FIG. 7 diagrammatically illustrates the electronic interconnection of various medical devices with the peripheral vascular lab (PVL) input/output (I/O) board and computer system in the examination unit.

FIG. 7 diagrammatically illustrates in greater detail the peripheral vascular lab PVL input/output board 221. This PVL I/O board 221 is substantially similar to the interconnection circuit 220 and the computer system for EU 212. The electrical interconnection between the remote control device 140, the processing unit 224 for the computer system 212 and the flying LCD display 17 (FIG. 1) is illustrated in FIG. 7. Additionally, FIG. 7 shows that audio mixer 232 is connected to headphone transmitter 233.

Figure 8A:
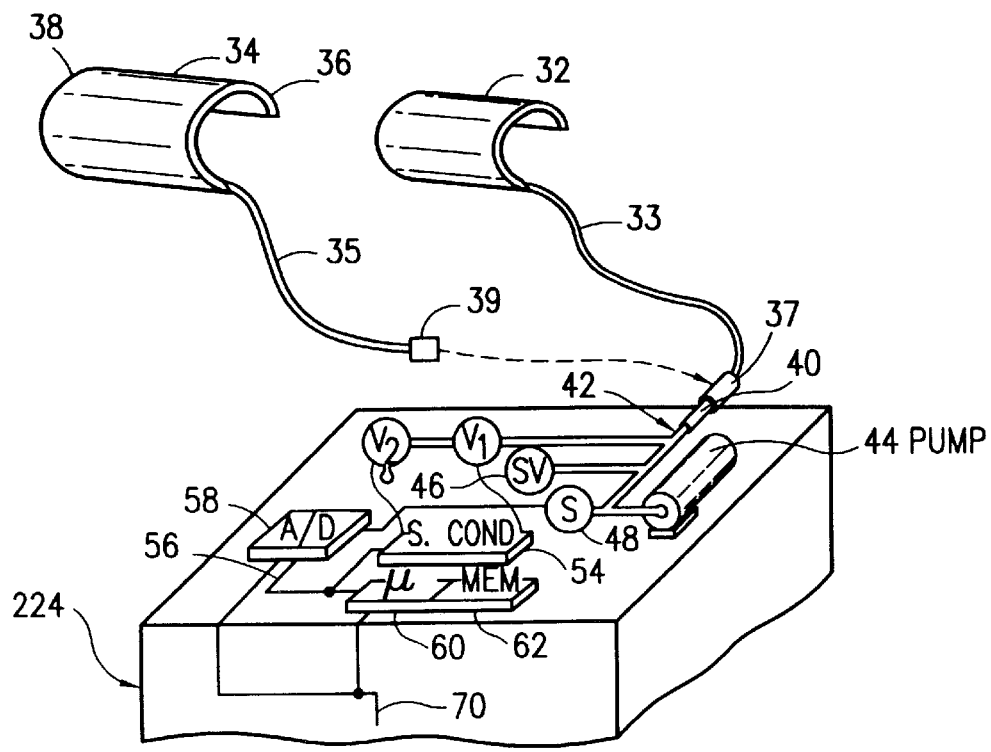
FIGS. 8A, 8B and 8C diagrammatically illustrate three embodiments of the internally calibrated PVR.
Figure 8B:
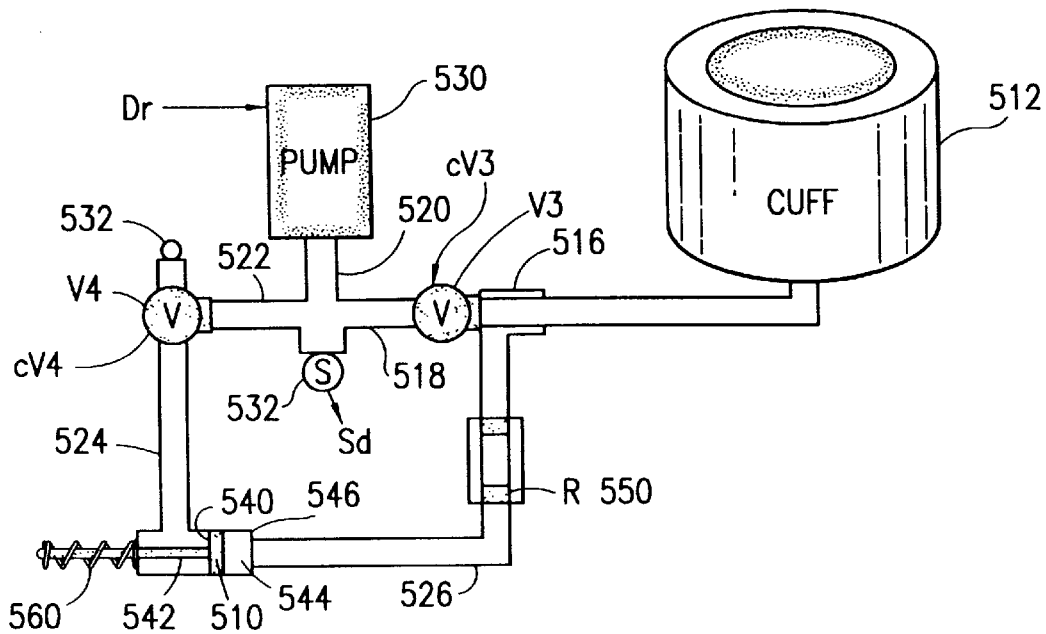
Figure 8C:
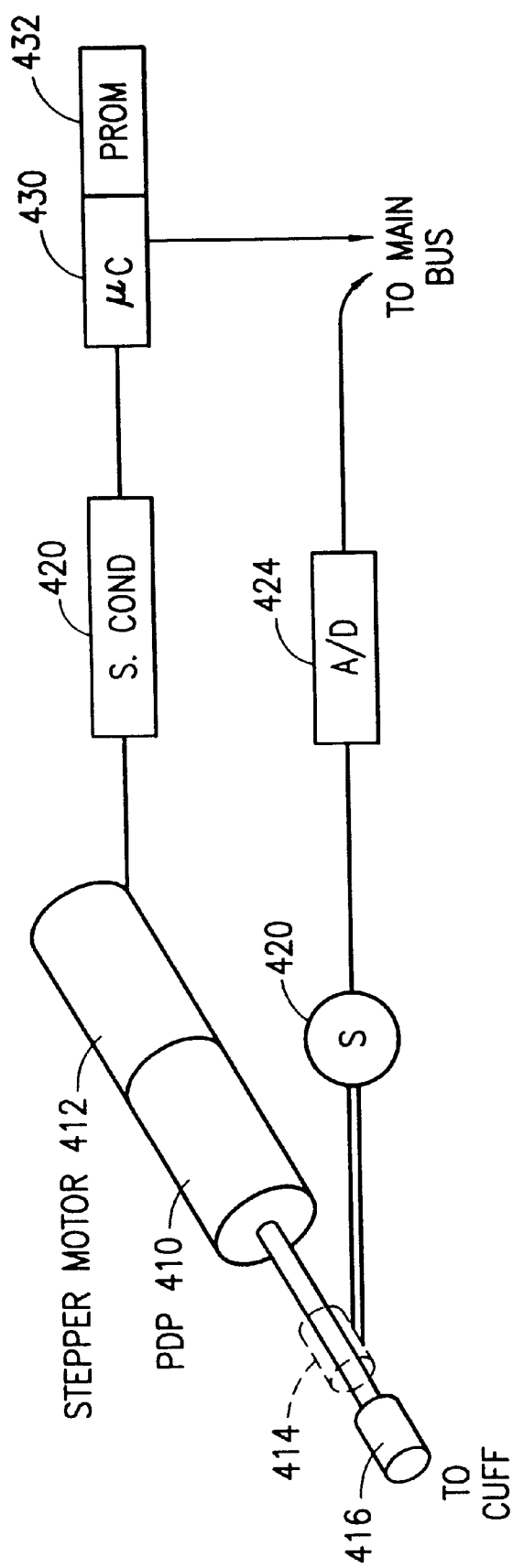

FIGS. 8A, 8B and 8C diagrammatically illustrate three different embodiments of the internally calibrated PVR. A further explanation of the internally calibrated PVR is found in U.S. patent application Ser. No. 08/484,933, filed Jun. 7, 1995 and U.S. patent application Ser. No. 08/608,825, filed Feb. 29, 1996. The contents of those two pending patent applications are incorporated herein by reference thereto.

FIG. 8A diagrammatically illustrates the hardware for one embodiment of the internal calibration for the PVR. In general, the calibration device is part of computer system 224. In FIG. 8A two pressure cuffs 32 and 34 are illustrated. Pressure cuff 32 is generally a cylindrical pressure cuff that is commonly used on an arm or a calf. In contrast, cuff 34 is a conical cuff such that proximal end 36 has a smaller diameter as compared with distal end 38 when the conical cuff is placed about the thigh of a patient. These cuffs are similar to those described earlier herein.

Each cuff has a coupling hose 33 and 35 and a pneumatic attachable coupler 37, 39 which attaches to a port 40. Port 40 is equivalent to the pneumatic ports on test port panel 47. The intervening valve assembly 214 is not shown in FIGS. 8A, 8A and 8C. Port 40 leads to a pneumatic system generally illustrated by tubes, couplers, hoses or pipes 42 which are inside the container of computer system 224.

Pneumatic internal coupling system 42 is connected to a pump 44, a valve $V_1$, a safety valve 46 (SV) and a pressure sensor 48 (S). Additionally, valve $V_1$ is pneumatically connected to a second valve $V_2$ via a closed chamber 50 having a pre-determined volume. The pre-determined volume in chamber 50 is about 1 ml. or 1 cc. Chamber 50 is a tube having an inside diameter of 4.5 mm and approximately 63 mm (2.48 inches) long. By maintaining valve $V_1$ closed while the cuff pressure in elevated to a predetermined level, (for example 70 mmHg), and then opening valve $V_1$ while maintaining valve $V_2$ closed, the volume in the closed pneumatic system (defined by substantially by the pressure cuff), is changed by a pre-determined volumetric amount. The electric signals, precisely representing pressure generated by pressure sensor 48 during the pneumatic calibration routine, provides a calibration signal which is used to calibrate the PVR or blood flow or volume monitoring system.

FIG. 8A also diagrammatically illustrates the general electrical components and electrical system connections for the computer system. For example, valves $V_1$, $V_2$, pump 44 are all supplied with power (the power lines are not shown) and control signals. The control signals are generally sent from signal conditioner 54 to the valves and the pump. Signal conditioner 54 is coupled to an internal bus 56. This internal bus (on the pressure sensor board) also carries data and control signals to and from and analog/digital (A/D) device 58. A/D 58 is electrically connected to pressure sensor S 48 as shown in FIG. 8A. Internal bus 56 is also connected to a micro controller 60 as well as a memory 62. Memory 62 may be a programmable read only memory (PROM) or other electronic device that stores computer programs. The code or micro code stored in memory 62 is utilized by micro controller 60 to drive, in conjunction with signal conditioner 54, valves $V_1$, $V_2$ and pump 44. Micro controller 60 also obtains, reviews and sends signals to and from A/D converter 58.

The output from A/D converter 58 is, as is known in the art, placed in a buffer and made available to other computer components via the main computer bus 70. This main computer bus is accessible to the central processor in computer system 224.

Upon opening valve V1, the closed pneumatic system primarily contained by pressure cuff 32, 34 experiences a change in volume by a predetermined amount. This predetermined amount is the interior size of the chamber defined by tube or cylinder 50. In one embodiment, this chamber and predetermined amount is 1 ml. The 1 ml volume change results in a change in the pressure signal, thereby causing the calibration pulse at a predetermined time. The calibration pulse is delivered at each discrete cuff pressure level. Accordingly, at cuff pressure levels 50, 60, 70, 80 . . . 160 during a peripheral vascular exam using the PVR, the system will generate a calibration pulse and change the volume in the closed pneumatic system by a predetermined amount of 1 ml.

FIG. 8B diagrammatically illustrates a pneumatic calibration system and the method for calibrating either a volume plethysmograph or a pulse volume recorder. It is the currently preferred embodiment of the ICPVR. The pneumatic calibration system illustrated in FIG. 8B includes a biased piston 510 that is utilized to change the volume by a predetermined amount in the closed pneumatic cuff system which includes cuff 512. The closed pneumatic system includes cuff 512, generally flexible hose 514, coupler port 516, and generally rigid tube sections 518, 520, 522, 524 and 526. The valve assembly 214 and test port panel 47 is omitted in FIG. 8B. Cuff valve $V_3$ is interposed between tube sections 516 and 518. On the outboard side, cuff 512 is pneumatically coupled to cuff valve $V_3$. On its inboard side, cuff valve $V_3$ is pneumatically coupled to tube sections 518, 520, 522 as well as pump 530 and pressure sensor S532. Pump 530 is driven by a drive signal Dr. Pressure sensor S532 generates a pressure sensor signal Sd. Exhaust valve $V_4$ is pneumatically coupled to tube sections 522 and 524. Exhaust valve $V_4$ is a two way valve wherein the exhaust port 532 of valve $V_4$ is normally closed but an interior passage links tube sections 522 and 524 together until the valve opens. When exhaust valve $V_4$ opens, air flow passes from the interior of tube section 524 and out of exhaust port 532. In other words, tube sections 518, 520, 522 and 524 are normally maintained at substantially the same high pressure level, that is, above the ambient pressure level. This high pressure level is equivalent to the discrete cuff pressure levels. This high pressure in the system is due to the injection of air into the closed pneumatic system by pump 530.

During normal operation when cuff 512 is pumped up to a discrete pressure level, exhaust valve $V_4$ is in a closed position (closed to exhaust port 532) and the air pressure in tube sections 518, 520, 522 and 524 affect the backside or rearface 540 of piston 542. Piston 542 moves within an interior space 544 of piston system 510 based upon a pressure differential between its rear and front faces. The piston is at a top position closest to terminal end 546 when cuff valve $V_3$ is open and valve $V_4$ has its exhaust port closed. Since valve $V_4$ is a two way valve, when that valve's exhaust port is closed, there is a fluid or pneumatic communication between tube segments 520, 522 and 524. Piston 542 is biased by a spring 560. Also during normal operation, that is, when cuff 512 is being pumped to or maintained at a discrete pressure level (for example 60 mmHg), the pressure in the system is substantially identical in tube segments 516, 518, 520, 522, 524, 526 and in piston chamber 544.

When the electronic components of the ICPVR issue a calibration trigger signal, cuff valve $V_3$ closes, exhaust valve $V_4$ opens to exhaust and piston 542 moves towards its bottom position thereby compressing spring 560 and adding approximately 1 ml of calibrated volume to the closed pneumatic system. In a preferred embodiment, 0.6 ml volume is added to the closed pneumatic system which includes cuff 512. The calibration trigger signal is, in reality, several electronic signals including control signal $cV_3$ applied to cuff valve $V_3$ and signal $cV_4$ applied to exhaust valve $V_4$. The signals are applied with the appropriate time delay in order to effectively isolate the cuff 512 prior to venting the backside of piston 542 and also to reduce jolts or undue transient changes in the closed pneumatic cuff system. When exhaust valve $V_4$ opens, piston 542 moves to a bottom position or away from terminal end 546 thereby adding a predetermined calibration volume to the closed pneumatic system. A flow restrictor R550 acts as a pneumatic damper for this change in volume.

Throughout this cycle, sensor S532 is substantially, continually generating pressure sensor signals Sd. These pressure sensor signals are applied to A/D converter 58 (FIG. 8A) and representative signals are applied to microcontroller 60 as well as processor 224. The Operation Table which follows summarizes the calibration method.

Operation Table

| Condition | Valve 3 (to cuff) | Valve 4 (to exhaust) | Piston |
|---|---|---|---|
| pump-up cuff | open | closed | top |
| at discrete P levels | open | closed | top |
| at cal. trigger | closed | open | bottom |
| post trigger time | open | closed | top |

In the current preferred embodiment, in order to move piston 542 to a top position, pump 530 is driven for a short period of time (by application of drive signal Dr) which causes an increase in pressure in the pneumatic calibration system after cuff valve $V_3$ is opened and the exhaust port on valve $V_4$ is closed. Since pressure sensor S532 continually monitors the pressure in the closed pneumatic cuff system (including cuff 512), the motor and pump 530 combination cycles on and off to maintain the pressure at the predetermined discrete pressure level (for example 80 mmHg) throughout that portion of the medical test. Tests have shown that there is no significant change in the pressure in the closed pneumatic system which includes cuff 512 when pump 530 is turned on for a short period of time to move piston 542 to its top position towards terminal end 546.

FIG. 8C diagrammatically illustrates another embodiment using a positive displacement pump (PDP) 410 driven by a stepper motor 412. This pump may include a piston which, at each cycle, injects a known volume of air into the pneumatic system. The internal pneumatic coupling system 414 includes a mechanical coupler 416 which can be attached pressure cuffs 32, 34, and particularly coupler lines 39 and 37 shown in FIG. 2. Pressure sensor 420 is also pneumatically connected to the internal pneumatic line 414. A/D converter 424 obtains and converts the signal from pressure sensor S 420. Signal conditioner 426 generates signals to control the stepper motor which in turn controls the positive displacement pump. Microcontroller 430 and memory PROM 432 control the A/D converter 424 as well as the stepper motor 412.

In operation, the positive displacement pump injects a certain amount of fluid or air into the cuff pressure based upon the number of turns stepper motor 412 delivers to the pump drive. Accordingly, a stepper motor driven to a certain level (a certain number of rotations) can drive a positive displacement pump to a certain level and inject a predetermined amount of volume of air into the closed pneumatic system at each cuff pressure level. This injection of a calibration volume of air into the system is used to calibrate the pneumatic gain at each discrete cuff pressure level as explained earlier. Instead of evacuating 1 ml of air, the stepper motor and PDP pump injects 1 ml of air into the system.

In addition to the ICPVR, the integrated peripheral vascular lab uses the following equipment.

Bi-directional Continuous-Wave Doppler

The selected bi-directional, continuous wave, doppler ultrasound system is a Hokanson Model MD6. It operates at a 5 MHz single frequency. This doppler weighs 9 ounces and is small enough to fit into a coat pocket. A high quality audio signal is provided by stereo earphones or a built-in speaker by the use of dynamic noise reduction circuitry. Direction of blood flow is perceived by the operator with stereo earphones; flow toward the probe is heard in the left ear and flow away is heard in the right. In addition to the audio signal, the operator can visually determine the direction of flow by red and green LEDs on the probe's end. An on/off switch is also located on the probe. The doppler ultrasound system uses rechargeable batteries with an automatic shutdown to prevent accidental battery drain. The doppler ultrasound has an analog output connection that normally allows it to be hooked to a separate chart recorder. In this integrated system, the chart recorder output is connected to the analog-digital converter board 221, via a plugjack to the test port panel 47 and the interconnection circuit 220.

Audiofrequency Analyzer (AA)

A microphone and a wireless radio frequency (RF) headphone set 61 supports the AA functions. There is a plug jack 112 at the test port panel 47 for the microphone electrical cord which will include the analog signal and ground. The analog signal is routed to the pre-amp on the interconnection circuit 220 which provides a 20 dB gain to the analog signal. The amplified analog signal is sent to the analog/digital converter board 218 where the signal is digitized and the results displayed graphically on the flat panel display 17. Also, the amplified signal is sent to the audio mixer 232 and from there is sent to the wireless RF 900 MHz headset transmitter 233. If the doppler ultrasound is being used by the operator, then the output of the pre-amp to the audio mixer for the microphone is grounded using the discrete input/output (I/O) capability of the analog/digital converter board, thereby disabling the audio output of the microphone.

Ocular Pneumoplethysmograph (OPG)

The OPG is an Electro-Diagnostic Instruments (EDI) model OPG-5D. It measures pressure in the ophthalmic artery. This functional measurement may be a predictor of significant extracranial carotid artery disease and its prognosis. The transducer 25 and its associated arm 27 is mounted on the end of the examination table 10 adjacent to the monitor swing arm 19. The footswitch 71 is wired to a connector in the base of the table.

Photoplethysmograph (PPG)

The PPG is a Hokanson Model MD6RP. The unit allows both AC and DC mode testing for all common PPG tests. The PPG includes an output that is normally used for sending data to a chart recorder and also as its power source. In this integrated system, the chart recorder output is connected to the analog-digital converter board 218, via a plug jack to the test port panel 47 and the interconnection circuit 220.

Figure 10:
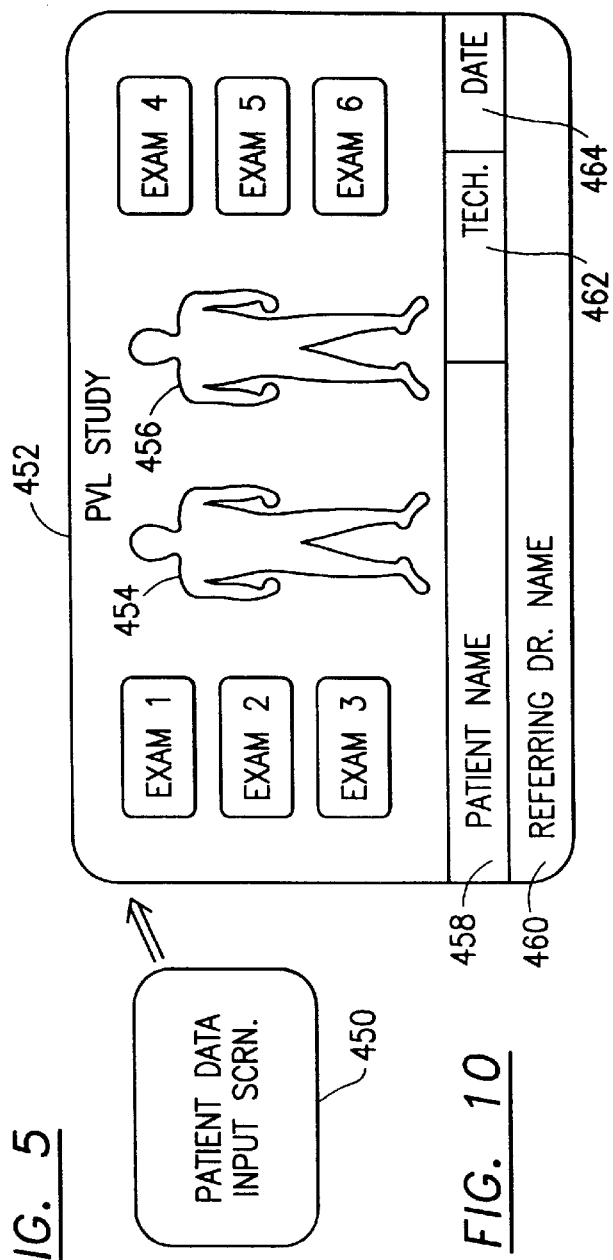
FIG. 10 diagrammatically illustrates two screen displays which are presented to the technician at the analyzing unit.

FIGS. 9, 11, 12 and 13 generally show basic flow charts for the basic AU program, the basic EU program, the generate report program and the review report program. FIG. 10 generally illustrates the user interface introduction into the review report or the generate report program.

AU Computer Software

The AU operating system is Microsoft Windows 95.

Applications software used with the AU computer is Microsoft Office Professional 95. It includes Microsoft Word word processing software, Microsoft Excel spreadsheet software, Microsoft Access relational database software, Microsoft PowerPoint presentation graphics software and Microsoft Schedule personal/group scheduling software.

AU Main Program

The AU main program software is based on Microsoft (MS) Access, a commercial off the shelf database management system. Data entry screens, report generation, and database update software will be written in Access Basic which interfaces directly with MS Access. Other software may be written in Borland C. The user interface is a standard Windows interface with user selections made with a point and click of a mouse.

Figure 9:
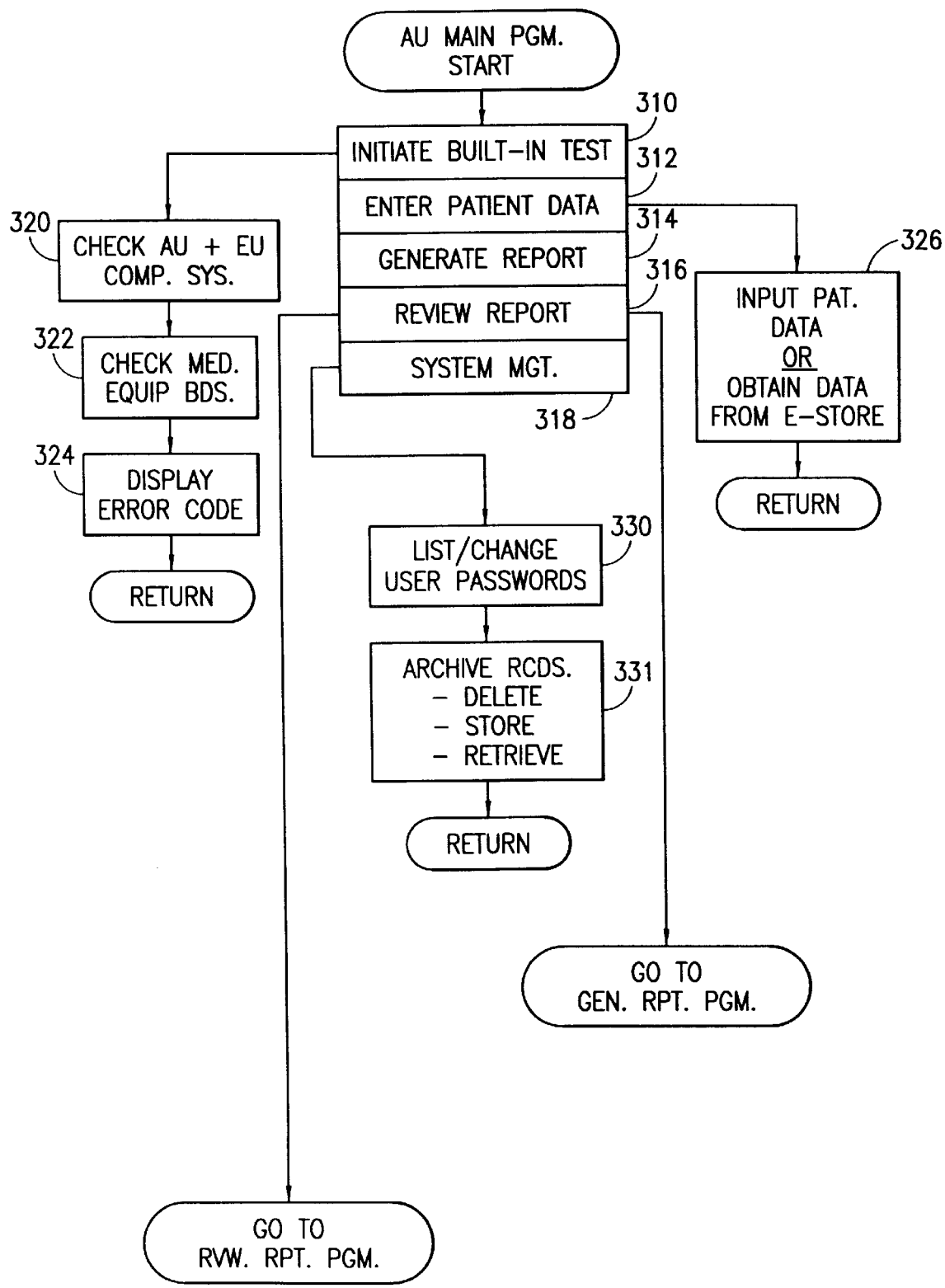
FIG. 9 diagrammatically illustrates a flow chart for the analyzing unit main program.

The AU software generally shown in FIGS. 9 and 10 consists of six major components: (1) user interface, (2) built-in test (BIT), (3) patient data entry, (4) report generation, (5) report review, and (6) system management.

AU User Interface

The user interface is normally controlled with a keyboard and mouse. On system powerup, an operator log-in screen is displayed. The operator then enters his unique identification code and password. If successful, then a Main Menu screen (see FIG. 9) is displayed which will give the user the option to (1) initiate BIT 310, (2) enter patient data 312, (3) generate report 314, (4) report 316, and (5) system management 318. The operator makes his selection with a point and click of the mouse. This results in a new set of menu options displayed. The user has the ability to return to the main menu from within any submenu.

Only those menu options available to a particular operator are displayed for any given menu. The options available are determined by his access level which is based on his unique identification code which is entered into the system through the System Management option of the AU software.

Built-In Test (BIT) Module

The AU initiates a BIT routine 310 to be executed on the instrument control system. The results are made available at the AU and are grenerally viewable on monitor 73 (FIG. 1). On powerup, BIT will be automatically executed. If a discrepancy is discovered, then a warning message describing the discrepancy will be displayed on the AU monitor. The operator has the option of initiating BIT at any other time after powerup. The results of each BIT is displayed on the console screen stored on the hard drive at the AU.

Step 320 checks the AU and the EU computer systems. Step 322 checks the medical equipment shown in the following table.

Check Medical Equipment Table
  Pump on ICPVR board
  Test all A/D converters
  Sample continuous wave doppler board
  Test OPG board
  Test remote control device
  In step 324, the error code is displayed, if necessary.

Patient Data Entry

The operator has the ability to enroll new patients into the AU database and can update/add data on patients currently enrolled into the AU. New patients are enrolled into the AU via a Patient Census Information Input Screen which includes name, age, sex and other general information. See step 326, FIG. 9.

Once the patient is enrolled into the database, the operator can then enter patient history, patient physical information, such as a blood pressure measurement or serum sample results, and other manual vascular exam results, performed by the technician at the EU. This data may be entered in via the keyboard and mouse or may be entered via computer readable media.

Report Generation

The operator has the ability to generate the following study reports (step 316, FIG. 9): (1) Complete Lower Extremity Venous Study Report, (2) Complete Lower Extremity Arterial Study Report, (3) Complete Extra Cranial Arterial Study Report, (4) Complete Upper Extremity Venous Study Report, and (5) Complete Upper Extremity Arterial Study Report. The study reports will be generated based on the data collected during the tests or vascular exams run on the EU.

Most of the information placed in the report is automatically imported from the EU, but some data requires user selections to be made. The technician, at the EU, collects several seconds of data which will include several heart cycles for the doppler ultrasound and audio analyzer, for example. The AU operator is able to display and listen to all of the recorded heart cycle data and then will select three cycles that best represent the vascular condition of the patient. The corresponding graphical representation of the selected heart cycles will be included in the study report.

Report Review

The operator has the ability to review any study report previously generated for a particular patient. When Report Review is selected, a list of patients with generated reports is displayed. Then, the operator selects a patient and a list of study reports for the particular patient will be displayed. Next, the operator selects a study report and then the study report is displayed. The operator may scroll through the report in any direction. Integrated with each report will be the corresponding sound data (analog versions of recorded digital instrument data) for items such as the doppler ultrasound and audio analyzer AA. The operator is able to click on a given sound and can hear what the technician heard at the EU. The operator can print the study report on the color printer at the AU.

System Management

When the operator selects System Management, two options are displayed: (1) User Passwords and (2) Data Archive. The User Password option permits the operator the ability to add/delete/modify user identifications, passwords and access levels. See step 330, FIG. 9.

Data Archive gives the operator the option of archiving patient data onto a back-up tape storage device, deleting patient data, and recalling patient data from a back-up tape. See step 331, FIG. 9.

Figure 13:
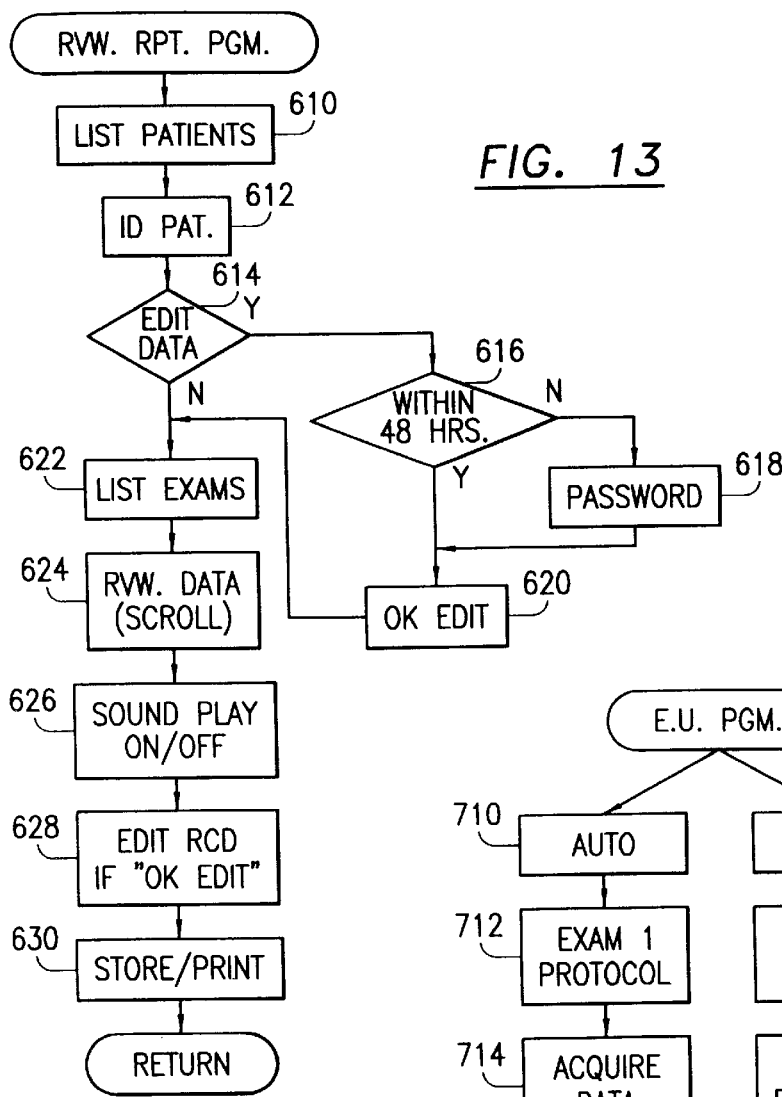
FIG. 13 diagrammatically illustrates a flow chart for the review report program.
Figure 12:
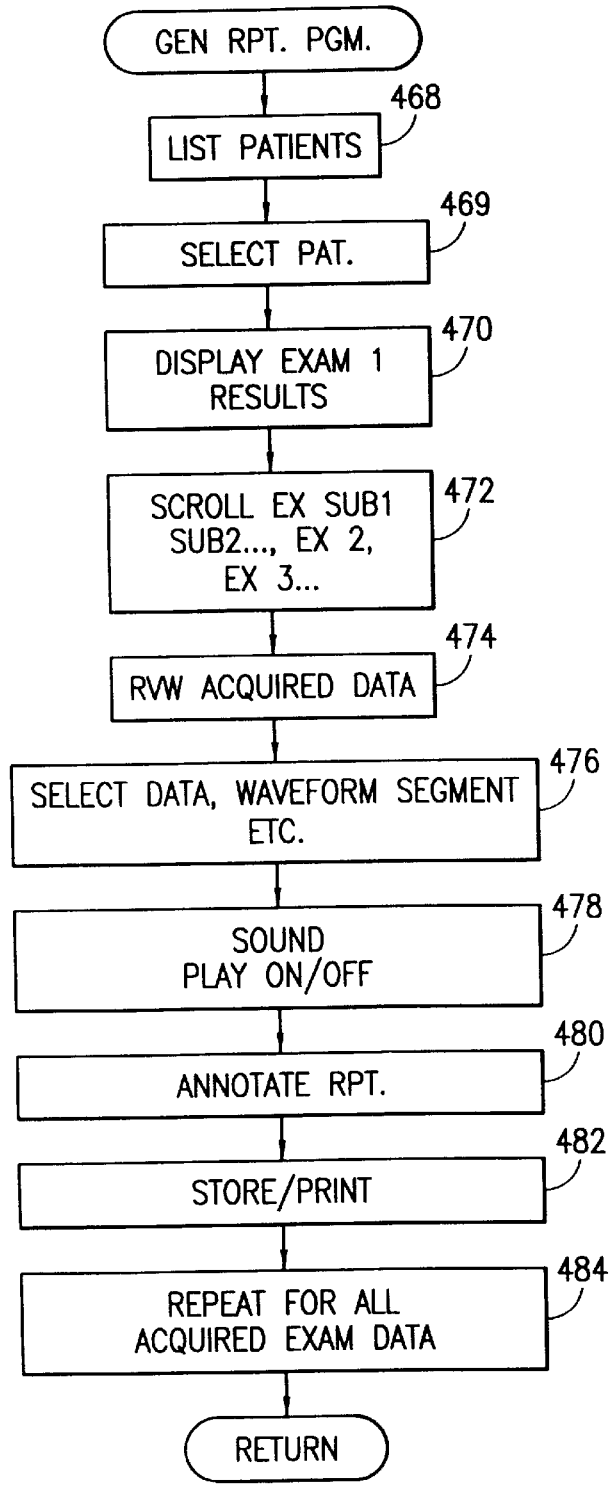
FIG. 12 diagrammatically illustrates a general flow chart for the generate report program.

FIGS. 12 and 13 generally provide flow charts for the generate report program (FIG. 12) and the review report program (FIG. 13).

In FIG. 10, screen display 450 prompts the technician to input patient data. The next screen display 452 graphically shows various vascular examinations (Exam 1–6), a front view 454 of a patient model and an anterior or back view 456 of a patient model. Additionally, the patient name is presented to the technician in area 458, the referring doctor is presented in area 460, the technician's name is presented in area 462 and the date is presented in area 464.

Returning to FIG. 12, the generate report program, in step 468, the technician is presented with a list of patients. He or she selects a patient from the list. This is noted in step 469. The technician is then presented with a display screen generally similar to that shown as display screen 452 in FIG. 10. The technician is presented with a selected exam results, in this case, vascular exam results 1 in step 470. The technician can scroll through exam subpart 1, subpart 2, as well as exam 2, and exam 3 in step 472. In step 474, the technician reviews the acquired data. This data is acquired at the examination unit as described later herein. In step 476, the technician selects a portion of the digital instrument data signal. For example, for the continuous wave doppler ultrasound exam, the technician will initially select about ten seconds of the ultrasound doppler at the examination unit. During the generate report program, the technical will select a three-second segment of that originally obtained ten second digital data signal.

In step 478, the technician can play back or listen to the ultrasound doppler signal. This is an analog version of the digital instrument data signals for the ultrasound doppler. In step 480, the technician can annotate the report. In step 482, the technician stores and/or prints the report on the color printer or on the hard drive of computer system 16 at analysis unit 12. In step 484, the technician repeats the program for all the acquired exam data.

FIG. 13 diagrammatically illustrates the review report program. In step 610, a list of patients is presented to the technician. In step 612, the technician selects one of the patients. Decision step 614 determines whether the technician wants to edit the data. If the YES branch is taken, a decision is made in step 616 whether the report was generated within the last 48 hours. If the report is more than 48 hours old, the NO branch is taken and the technician must input his or her password in accordance with step 618. If the password is not cleared for editing the report more than 48 hours old, the program stops. If the password is cleared, or if the report was created within the last 48 hours, the YES branch is taken from decision step 616 and in step 620 the OK edit command code is set. The program returns to a point on the NO branch from the edit data decision step 614. In step 622, the technician is presented with all vascular exams compiled for that patient. In this manner, the program may call up a display screen similar to that shown in display screen 452 in FIG. 10. In step 624, the technician can scroll through the exam data. In step 626, the technician can turn on and off the analog playback device. In this manner, the technician can hear the ultrasound doppler signals or the audio frequency analyzer AA signals. In step 628, the technician is permitted to edit the record if the OK edit command bit is properly set. In step 630, the technician may store and/or print the report.

Figure 11:
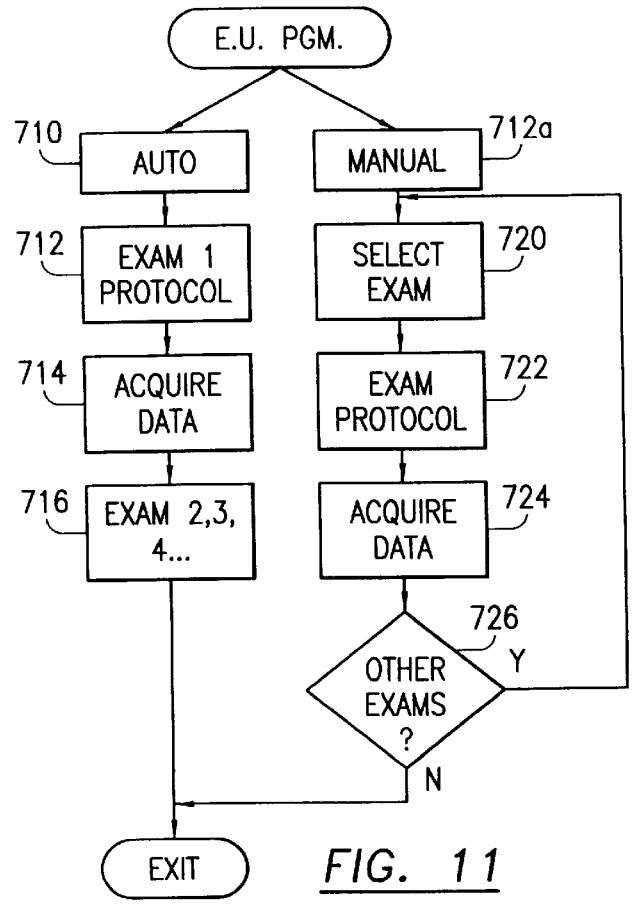
FIG. 11 diagrammatically illustrates a top level flow chart for the operation of the examining unit program.

FIG. 11 generally provides a flow chart for the examination unit or EU program. The program can be run on automatic as noted by step 710 or may be run in a manual mode as noted by step 712. In an automatic presentation, the EU computer system steps the operator through a predetermined number of vascular exams. Accordingly, in step 712, vascular exam 1 protocol is shown on flying display monitor 17. The technician uses remote control device 41 to select instrument data signals and the computer system in the EU 10 records those signals as digital instrument data signals. Step 714 recognizes that the technician is selecting digital data signals as well as inputting keypad entry data into the RCD 41. Step 716 indicates that the vascular exam proceeds through exams 2, 3, 4 until the program exits.

In a manual mode, the operator in step 720 selects which vascular exam he or she is going to conduct on patient 23. In step 722, the exam protocol is displayed on display monitor 17. Control commands and keypad entry data are input by the technician in RCD 41. For long data entry, the technician may utilize keyboard 75 at the analysis unit 12.

Step 724 recognizes that the technician will acquire instrument data signals as well as keypad entry data. Decision step 726 determines whether other vascular exams will be conducted on patient 23. If so, the program reverts to a point preceding select exam step 720. If not, the NO branch is taken and the program exits.

The following paragraphs describe in greater detail the software running on the EU computer. This software allows the operator to select and run one or more vascular studies, select a particular diagnostic test, and to execute a built-in test (BIT) of the components at the EU station.

The user interface software at the EU:(1) interprets selections made from the RCD 41 and then executes the appropriate function based on the selection made; (2) generates a graphical representation of the instrument data as it is collected on the flat panel display 17, equivalent to a chart recorder hard copy; (3) records the data collected during a study on the AU hard drive in computer system 16 to be used to generate the study reports; and (4) selects the appropriate audio output generated from either the doppler or the Audio Analysis AA system and feeds it to the technician's head-set 61.

After power-up and after the completion of a study, the EU will be in a mode waiting for (1) a request from the AU to perform the next patient study; (2) for a selection from the technician to enter the free-play or manual mode; or (3) for a selection from the technician to run the built-in test. If a patient study is to be performed, then the EU will execute the appropriate study control software module which will step the technician through the study with visual prompts from monitor 17 and lights on RCD 41. These modules are described earlier herein. If the technician selects free-play or manual mode, then any instrument can be selected and the appropriate audio and video outputs will be generated using the appropriate instrument routine.

If BIT is selected from the AU or EU, then a series of diagnostic tests are executed. These tests include a calibration of the OPG and verifying communication with the PVR and the A/D board. If the last BIT indicated that some part of the equipment at the station was not functioning within specified parameter limits, then the user interface module displays all studies requiring the use of that equipment in a different graphical format, indicating that they are not currently available. Once the BIT indicates that the equipment has returned to an operational status, the studies will again be displayed as "available." BIT will always appear as an available option.

The BIT routine performs a basic functionality check on the equipment connected to the EU system. It displays the items being tested on screen and indicates a pass/fail condition for each item tested. The results are also written to a log file with a name that includes the date on which the test was performed. In addition, the test results are written to a standard file location (overwriting previous results), which the user interface module may check to determine which options are available.

Study Control

The study control modules are the seven highest level modules executable in the EU. The seven available studies are as follows:

Study Table

Lower Extremity Arterial Study (LEAS)
   Lower Extremity Venous Study (LEVS)
   Upper Extremity Arterial Study (UEAS)
   Upper Extremity Venous Study (UEVS)
   Extracranial Arterial Study (EAS)
   Male Impotence Study (MIS or MI Study)
   Miscellaneous Studies Each of the seven studies will electronically call some combination of the instrument modules described below.

LEAS

The LEAS will collect the data required for the LEAS report, using the lower PVR routine and the lower blood pressure routine.

The lower PVR module controls the lower PVR vascular exam or test. The operator is directed to place the cuffs in the appropriate place for a lower extremities test. The lower PVR test module directs the PVR hardware to inflate the cuff. The lower PVR module then calibrates the PVR. This internal calibration is discussed earlier herein. After the PVR has been calibrated, the lower PVR module samples the cuff pressure and transfers the digitized data to the EU system. PVR results are graphed in real time on the display during data acquisition. The digitized instrument data is stored.

The lower blood pressure or LBP module directs the LBP test. The operator is directed to place the cuffs and doppler probe in the appropriate area for a lower extremities test. The PVR hardware is directed to inflate the cuff to a predetermined pressure to occlude the vein. The PVR outlet valve is opened to reduce the pressure quickly. When the doppler probe detects blood flow, the operator selects "record blood pressure" from the RCD and the instrument data signal is recorded.

LEVS

The LEVS collects the data required for the LEVS report, using the lower PVR routine and the lower venous doppler routine. The lower PVR routine is discussed above.

The lower venous doppler ultrasound or LVD module directs the LVD test. The operator is directed to place the doppler probe in the appropriate area for a lower extremities venous test. The A/D driver module is directed to sample the output of the doppler probe electronics. The digitized instrument data is then stored.

UEAS

The UEAS collects the data required for the UEAS report, using the upper PVR routine and the upper blood pressure routine respectively.

The upper PVR module directs the upper PVR test. The operator is directed to place the cuffs in the appropriate place for an upper extremities test. The upper PVR test module directs the PVR hardware to inflate the cuff. The upper PVR module then calibrates the PVR. After the PVR has been calibrated, the upper PVR module samples the cuff pressure and transfers the digitized data to the EU system. PVR results are graphed on the display 17 and the digitized data is stored.

The upper blood pressure or UBP module directs the UBP test. The operator is directed to place the cuffs and doppler probe in the appropriate area for an upper extremities test. The PVR hardware is directed to inflate the cuff to a predetermined pressure to occlude the vein. The PVR outlet valve is opened to reduce the pressure quickly. When the doppler probe detects blood flow, the operator selects "record blood pressure" from the RCD 41 and the signal is recorded.

UEVS

The UEVS collects the data required for the UEVS report, using the upper PVR routine and the upper venous doppler routine. The upper PVR routine is discussed above.

The upper venous doppler ultrasound or UVD module directs the UVD test. The operator is directed to place the doppler probe in the appropriate area for an upper extremities venous test. The A/D driver module is directed to sample the output of the doppler probe electronics. The digitized data is then stored.

EAS

The EAS collects the data required for the EAS report, using the upper blood pressure routine discussed above, the OPG routine, and the AA routine.

The OPG module directs the OPG test. The operator is directed to perform the test according to manufacturer specifications. The A/D driver module is directed to sample the output of the OPG electronics. The OPG results are graphed on the display 17 and the digitized data is stored.

The audio analysis AA module directs the audio analysis test. The operator is directed to place the sensitive AA microphone in the appropriate area for an audio analysis test. The A/D driver module is directed to sample the output of the Audio Analysis electronics. The audio analysis results are graphed on the display 17 and the digitized data is stored.
MI Study The male impotence or MI Study collects the data required for the MI Study report, using the Mean Penile Arterial Perfusion Pressure routine and the Biothesiometry routine.

The mean penile arterial perfusion pressure or MPPP module directs the MPPP test. The operator is directed to place the cuff in the appropriate area on the penis to take the MPPP measurement and the penile systolic pressure measurement. The MPPP measurement is the maximum amplitude of the PVR samples taken at predefined intervals of cuff pressure. The penile systolic pressure measurement is taken by the PVR hardware which is directed to inflate the cuff to a predetermined pressure. When the valve is opened slowly, the point where blood flow is recorded is the penile systolic pressure. The MPPP results are graphed on the display and the measurement data is stored. Other calculated measurements, based on the MPPP and penile systolic pressure data, are stored.

The Biothesiometry module directs the Biothesiometry test. The operator is directed to take 5 measurements using a separate hand-held device. The operator enters the measurements that are displayed via keypad entry and this data is stored. The measurement values are compared to the normal range of values and an indication of "normal" or "abnormal" is displayed.
Miscellaneous Studies The Miscellaneous Studies allow the operator to use a specific instrument at a specific area on the patient, e.g., perform a PVR measurement on the patient's left ankle. This routine calls the respective instrument routine as described herein.

The following are additional lower and upper extremity tests. The lower PPG module directs the LPPG test. The operator is directed to place the PPG in the appropriate area for a lower extremities PPG test. The A/D driver module is directed to sample the output of the PPG electronics. The PPG results are graphed on the display and the digitized data is stored.

The upper PPG module directs the UPPG test. The operator is directed to place the PPG in the appropriate area for an upper extremities PPG test. The A/D driver module is directed to sample the output of the PPG electronics. The PPG results are graphed on the display and the digitized data is stored.
Data Formatting The data formatting routines convert/translate the raw data received from the instrument routines into various disk storage formats. Data from all instruments is stored in tabular ASCII format. No processing is performed on the data by these routines. Data selection and manipulation are performed during report generation at the AU system.

Figure 14:
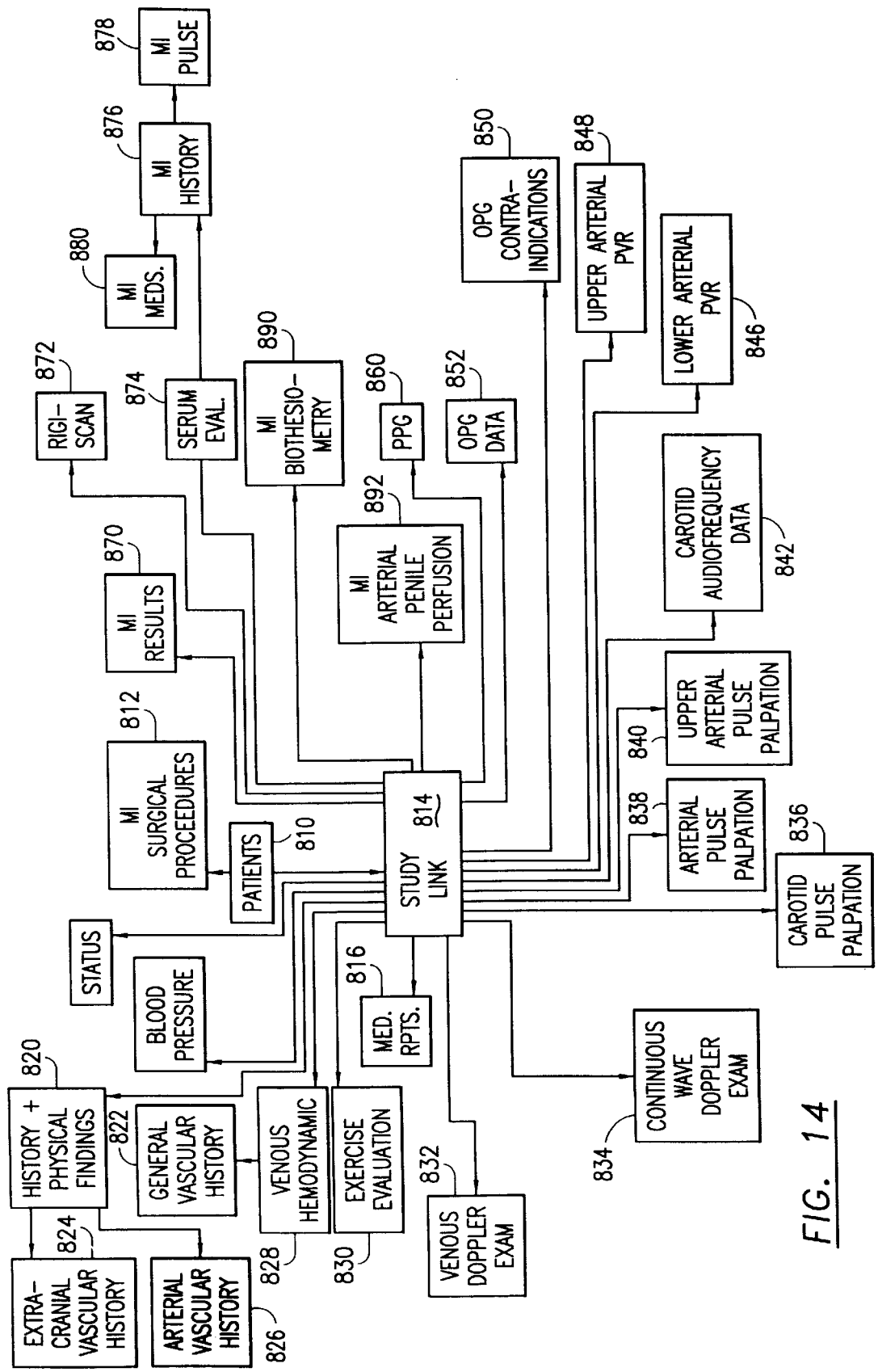
FIG. 14 diagrammatically illustrates an entity relationship diagram for the peripheral vascular diagnostic lab and system.

FIG. 14 diagrammatically illustrates the peripheral vascular lab PVL entity relationship diagram. The arrows in FIG. 14 indicate hierarchy or priority for those data functions. For example, with respect to patient block 810, data must be entered into that functional routine prior to initiating male impotence MI surgical procedures 812 and prior to initiating study link 814. The patient functional block includes the following information:

Patients
    SSN/Patient ID: Text(11)
    LastName: Text(50)
    FirstName: Text(50)
    MI: Text(1)
    Sex: Text(1)
    Date Entered: Date/Time
    DOB: Date/Time
    PriorEvaluation: Date/Time This patient entry function includes keypad entry data representing the patient's social security number, his or her last name, first name, middle initial identifier (a single bit of text), sex, date and time, date of birth and date of prior evaluation.

The study link functional block 814 includes the following items:
Study Link
    SSN/Patient ID: Text(11)
    Date/Time: Date/Time
    Referring Physician: Text(50)
    Examined By: Text(50)
    Report Code: Text(15)
    Word File Path: Text(50)
    Analyzed Data: Yes/No Study link functional block 814 has priority or is superior over the medical reports functional block 816. The medical reports block includes the following information:
Medical Reports
    Report Code: Text(15)
    Report Name: Text(50)
    Corr Form Name: Text(70)

The information in the history and physical findings functional block 820, the general vascular history functional block 822, the extracranial vascular history block 824 and the arterial vascular history functional block 826 are all entered via the keypad in a keypad entry data. The information entered via keyboard 75 on analysis unit 12 or RCD keypad 41 is identified in the following tables:
History and Physical Findings
    SSN/Patient ID: Text(11)
    Date/Time: Date/Time
    Recent Trauma Right: Text(2)
    Recent Trauma Left: Text(2)
    Edema Right: Text(2)
    Edema Left: Text(2)
    Calf Tenderness Right: Text(2)
    Calf Tenderness Left: Text(2)
    Arm Tenderness Right: Text(2)
    Arm Tenderness Left: Text(2)
    Skin Changes Right: Text(2)
    Skin Changes Left: Text(2)
    Varicose Veins Right: Text(2)
    Varicose Veins Left: Text(2)
    Previous DVY Right Upper: Text(2)
    Previous DVY Left Upper: Text(2)
    Previous DVY Right Lower: Text(2)
    Previous DVY Left Lower: Text(2)
    Pleural Discomfort: Text(2)
    Hormone Use: Text(2)
    Hypercoagulability: Text(2)

Malignant Disease: Text(2)
CVA: Text(2)
CHF: Text(2)
Other: Text(2)
S/P and Notes: Memo
General Vascular History
   SSN/Patient ID: Text(11)
   Date/Time: Date/Time
   Cigarette Smoking: Text(10)
   Hypertension: Text(2)
   Diabetes: Text(9)
   Hypertipidemia: Text(2)
   Obesity: Text(2)
   Angina: Text(2)
   MI: Text(2)
   CVA: Text(2)
   Claudication: Text(2)
   Headache: Text(2)
   Dysphasia: Text(2)
   Syncope: Text(2)
   Vertigo: Text(2)
   Dizziness: Text(2)
   Amaurosis Fugax: Text(2)
   Hemiplegia: Text(2)
   Asymptomatic: Text(2)
   TIA: Text(2)
   S/P and Notes: Memo
   Vascular Skin Lesions: Text(200)
   Resting Symptoms: Text(200)
   Exertional Symptoms: Text(200)
Extracranial Vascular History
   SSN/Patient ID: Text(11)
   Date/Time: Date/Time
   Claudication: Text(2)
   Headache: Text(2)
   Dysphasia: Text(2)
   Syncope: Text(2)
   Vertigo: Text(2)
   Dizziness: Text(2)
   Amaurosis Fugax: Text(2)
   Hemiplegia: Text(2)
   Asymptomatic: Text(2)
   TIA: Text(2)
   S/P and Notes: Memo
Arterial Vascular History
   SSN/Patient ID: Text(11)
   Date/Time: Date/Time
   Vascular Skin Lesions: Text(200)
   Resting Symptoms: Text(200)
   Exertional Symptoms: Text(200)
   S/P and Notes: Memo In contrast to functional blocks 820–826, the venous hemodynamic functional block 828 stores both a keypad entry data as well as waveform data or digital instrument data signals obtained from the pulse volume recorder PVR.

Venous Hemodynamic
   SSN/Patient ID: Text(11)
   Date/Time: Date/Time
   Right MVO: Double
   Left MVO: Double
   Right SVC: Double
   Left SVC: Double Particularly, a directory on the computer system is made for each patient. In this directory, text data is put in certain files. Other files hold waveform data in various subdirectories. This waveform data or other types of digital instrument data signals are linked to the keypad entry data with the appropriate electronic linkage commands.

The exercise evaluation functional block 830 includes the following keypad entry data:

Exercise Evaluation
   SSN/Patient ID: Text(11)
   Date/Time: Date/Time
   Maximum Walking Time: Single
   Rate: Single
   Grade: Single
   Symptoms with Exercise: Memo
   Symptoms at Time1: Single
   Symptoms at Time2: Single
   Symptoms at Time3: Single
   Symptoms 1: Memo
   Symptoms 2: Memo
   Symptoms 3: Memo
   Right Bilateral Ankle Sys Pressure: Text(5)
   Left Bilateral Ankle Sys Pressure: Text(5)
   Brachial Systolic Pressure: Text(5)
   Right Femoral Bruits: Yes/No
   Left Femoral Bruits: Yes/No The venous doppler exam functional block 832 includes a reasonably large amount of digital instrument data signals. As discussed earlier, the doppler ultrasound probe detects blood flow through veins and arteries of the patient. Upon the proper command by the technician, the digital instrument data signals obtained from the analog doppler signals are initially stored in the examination unit. The venous doppler exam table set forth below identifies data fields. As is common, a byte is an 8-bit data field.

Venous Doppler Exam
   SSN/Patient ID: Text(11)
   Date/Time: Date/Time
   Common Femoral Spontaneous R: Byte
   Common Femoral Spon taneous L: Byte
   Common Femoral Phasic R: Byte
   Common Femoral Phasic L: Byte
   Common Femoral Augmented R: Byte
   Common Femoral Augmented L: Byte
   Common Femoral Competent R: Byte
   Common Femoral Competent L: Byte
   Common Femoral Nonpulsable R: Byte
   Comm on Femoral Nonpulsable L: Byte
   Popliteal Spontaneous R: Byte
   Popliteal Spon taneous L: Byte
   Popliteal Phasic R: Byte
   Popliteal Phasic L: Byte
   Popliteal Augmented R: Byte
   Popliteal Augmented L: Byte
   Popliteal Competent R: Byte
   Popliteal Competent L: Byte Popliteal Nonpulsable R: Byte
Popliteal Nonpulsable L: Byte
Posterior Tibial Spontaneous R: Byte
Posterior Tibial Spontaneous L: Byte
Posterior Tibial Phasic R: Byte
Posterior Tibial Phasic L: Byte
Posterior Tibial Augmented R: Byte
Posterior Tibial Augmented L: Byte
Posterior Tibial Competent R: Byte
Posterior Tibial Competent L: Byte
Posterior Tibial Nonpulsable R: Byte
Posterior Tibial Nonpulsable L: Byte
Superficial Femoral Spontaneous R: Byte
Superficial Femoral Spontaneous L: Byte
Superficial Femoral Phasic R: Byte
Superficial Femoral Phasic L: Byte
Superficial Femoral Augmented R: Byte
Superficial Femoral Augmented L: Byte
Superficial Femoral Competent R: Byte
Superficial Femoral Competent L: Byte
Superficial Femoral Nonpulsable R: Byte
Superficial Femoral Nonpulsable L: Byte
Greater Saphenous Spontaneous R: Byte
Greater Saphenous Spontaneous L: Byte
Greater Saphenous Phasic R: Byte
Greater Saphenous Phasic L: Byte
Greater Saphenous Augmented R: Byte
Greater Saphenous Augmented L: Byte
Greater Saphenous Competent R: Byte
Greater Saphenous Competent L: Byte
Greater Saphenous Nonpulsable R: Byte
Greater Saphenous Nonpulsable L: Byte
Brachial Spontaneous R: Byte
Brachial Spontaneous L: Byte
Brachial Phasic R: Byte
Brachial Phasic L: Byte
Brachial Augmented R: Byte
Brachial Augmented L: Byte
Brachial Competent R: Byte
Brachial Competent L: Byte
Brachial Nonpulsable R: Byte
Brachial Nonpulsable L: Byte The continuous wave doppler function 834 also stores digital representations of the instrument data signal obtained from the doppler probe.

Continuous Wave Doppler Exam
SSN/Patient ID: Text(11)
Date/Time: Date/Time
Supraorbital Left: Integer
Supraorbital Right: Integer
Temporal Compression Left: Integer
Temporal Compression Right: Integer
Facial Compression Left: Integer
Facial Compression Right: Integer
Proximal Left: Integer
Proximal Right: Integer
Distal Left: Integer
Distal Right: Integer Commonly, the technician will initially select about ten seconds of the doppler signal. He or she does this by listening to the playback of the analog signals on headset 61. When the technician finds an acceptable signal, he or she selects the record button on RCD 41. The computer system in the examining unit then records about ten seconds of that signal. Simultaneously, that signal may be displayed on flying monitor 17. After the exam is completed, the technician then goes to analyzing unit 12. While generating the report with keypad 75 and monitor 73, the technician can listen to that ten second initially acquired signal and further select three seconds of the continuous wave doppler signal. It is that three second signal that is electronically linked with the vascular diagnostic reports. As discussed later herein, the electronic version of the vascular diagnostic report as well as the digital representation of that analog doppler signal can be transmitted across a telecommunications network. This enables the referring physician to not only see the electronic version or the printed out version of the report, but also hear the analog version of the recorded doppler exam. This ability to record not only text and integrate the keypad entry data along with the digital representation of the analog is an important feature of the present invention.

The carotid pulse palpation function step 836, the arterial pulse palpation step 838, and the upper arterial pulse palpation function 840 are all essentially keypad entry data.

Carotid Pulse Palpation
SSN/Patient ID: Text(11)
Date/Time: Date/Time
Common Carotid Right: Text(10)
Common Carotid Left: Text(10)
Temporal Right: Text(10)
Temporal Left: Text(10)
Facial Right: Text(10)
Facial Left: Text(10)
Carotid Bruits Right: Yes/No
Carotid Bruits Left: Yes/No
Temporal Bruits Right: Yes/No
Temporal Bruits Left: Yes/No
Facial Bruits Right: Yes/No
Facial Bruits Left: Yes/No Arterial Pulse Palpation
SSN/Patient ID: Text(11)
Date/Time: Date/Time
Femoral Right: Text(3)
Femoral Left: Text(3)
Popliteal Right: Text(3)
Popliteal Left: Text(3)
Anterior Tibial Right: Text(3)
Posterior Tibial Right: Text(3)
Anterior Tibial Left: Text(3)
Posterior Tibial Left: Text(3)
Femoral Bruits Right: Yes/No
Femoral Bruits Left: Yes/No
Femoral Doppler Right: Integer
Femoral Doppler Left: Integer
Popliteal Doppler Right: Integer
Popliteal Doppler Left: Integer
Anterior Tibial Doppler Right: Integer
Posterior Tibial Doppler Right: Integer Anterior Tibial Doppler Left: Integer
Posterior Tibial Doppler Left: Integer
Upper Arterial Pulse Palpation
    SSN/Patient ID: Text(11)
    Date/Time: Date/Time
    Carotid Pulse Left: Text(3)
    Carotid Pulse Right: Text(3)
    Subclavian Pulse Left: Text(3)
    Subclavian Pulse Right: Text(3)
    Axiliary Pulse Left: Text(3)
    Axiliary Pulse Right: Text(3)
    Brachial Pulse Left: Text(3)
    Brachial Pulse Right: Text(3)
    Radial Pulse Left: Text(3)
    Radial Pulse Right: Text(3)
    Ulnar Pulse Left: Text(3)
    Ulnar Pulse Right: Text(3)
    Carotid Bruits Left: Yes/No
    Carotid Bruits Right: Yes/No
    Subclavian Bruits Left: Yes/No
    Subclavian Bruits Right: Yes/No
    Carotid DS Left: Integer
    Carotid DS Right: Integer
    Subclavian DS Left: Integer
    Subclavian DS Right: Integer
    Axiliary DS Left: Integer
    Axiliary DS Right: Integer
    Brachial DS Left: Integer
    Brachial DS Right: Integer
    Radial DS Left: Integer
    Radial DS Right: Integer
    Ulnar DS Left: Integer
    Ulnar DS Right: Integer The carotid audio frequency data function 842, the lower arterial PVR function 846 and the upper arterial PVR function 848 involve the storage of keypad entry data, but primarily involve the storage of digital versions of waveforms corresponding to sound or audio (for the audio frequency data) or waveforms in the form of the electronic output of a PVR.

Carotid Audiofrequency Data
    SSN/Patient ID: Text(11)
    Date/Time: Date/Time
    Cardiac Murmur: Yes/No
    Subclavian Bruit: Yes/No
    CAA1 Right: Yes/No
    CAA2 Right: Yes/No
    CAA3 Right: Yes/No
    CAA4 Right: Yes/No
    CAA5 Right: Yes/No
    CAA1 Left: Yes/No
    CAA2 Left: Yes/No
    CAA3 Left: Yes/No
    CAA4 Left: Yes/No
    CAA5 Left: Yes/No
Lower Arterial PVR
    SSN/Patient ID: Text(11)
    Date/Time: Date/Time
    Right Thigh Psys: Text(5)
    Left Thigh Psys: Text(5)
    Right Calf Psys: Text(5)
    Left Calf Psys: Text(5)
    Right Ankle Psys: Text(5)
    Left Ankle Psys: Text(5)
Upper Arterial PVR
    SSN/Patient ID: Text(11)
    Date/Time: Date/Time
    Right Upper Arm Psys: Integer
    Left Upper Arm Psys: Integer
    Right Forearm Psys: Integer
    Left Forearm Psys: Integer The OPG contraindications function block 850 is a text based date entry and the OPG data function block 852 is a waveform or digital representation of an analog signal data entry.

OPG Contraindications
    SSN/Patient ID: Text(11)
    Date/Time: Date/Time
    Contraindications: Yes/No
    Glaucoma: Yes/No
    Conjunctivitis: Yes/No
    Eye Trauma: Yes/No
    Allergic: Yes/No
OPG Data
    SSN/Patient ID: Text(11)
    Date/Time: Date/Time
    Ophthalmic Artery Left: Integer
    Ophthalmic Artery Right: Integer The PPG function block 860 represents both text but primarily waveform data.

PPG
    SSN/Patient ID: Text(11)
    Date/Time: Date/Time
    PPG Location: Text(50)

The male impotence MI function blocks are: MI surgical procedures 812, MI results 870, RigiScan function 872, serum evaluation 874, MI history 876, MI pulse 878 and MI medications 880 as well as MI biothesiometry 890 and MI arterial penile perfusion 892. These are currently keypad data entry. However, the MI arterial penile perfusion is a keypad entry or single number which is calculated based upon certain PVR values. This is discussed above in connection with the corresponding module.

MI Surgical Procedures
    SSN/Patient ID: Text(11)
    Date/Time: Date/Time
    Procedure Name: Text(200)
MI Results
    SSN/Patient ID: Text(11)
    Date/Time: Date/Time
    Medical Consistent: Text(3)
    Sexual History Consistent: Text(3)
    RigiScan Findings: Text(3)
    Arterial Penile Perfusion Measurements: Text(3)
    Biothesiometry Results: Text(3)
    Serum Evaluation: Text(3)
RigiScan
    SSN/Patient ID: Text(11)

Date/Time: Date/Time
Date 1: Date/Time
Date 2: Date/Time
Time 1: Single
Time 2: Single
Number of events 1: Text(15)
Number of events 2: Text(15)
Resting Tumescence 1: Text(7)
Resting Tumescence 2: Text(7)
Tip Increase 1: Text(7)
Tip Increase 2: Text(7)
Base Increase 1: Text(7)
Base Increase 2: Text(7)
Max Duration 1: Integer
Max Duration 2: Integer
Average Duration 1: Integer
Average Duration 2: Integer
Max Rigidity 1: Integer
Max Rigidity 2: Integer
Dissociation 1: Integer
Dissociation 2: Integer
Uncoupling 1: Integer
Uncoupling 2: Integer
Plots Attached: Yes/No
Serum Evaluation
  SSN/Patient ID: Text(11)
  Date/Time: Date/Time
  Glucose Fasting: Integer
  TST: Integer
  Prolactin: Double
  LH: Double
  Lab: Text(25)
  Office: Text(25)
  Other: Text(25)
MI Biothesiometry
  SSN/Patient ID: Text(11)
  Date/Time: Date/Time
  MI Age: Byte
  1st Digit Right: Byte
  1st Digit Left: Byte
  Shaft Right: Byte
  Shaft Left: Byte
  Glans: Byte
MI Medications
  SSN/Patient ID: Text(11)
  Date/Time: Date/Time
  Name: Text(100)
  Dose: Text(50)
  When Taken: Text(50)
MI Arterial Penile Perfusion
  SSN/Patient ID: Text(11)
  Date/Time: Date/Time
  MPPP: Integer
  Penile Systolic Pressure: Integer
  PVR Amplitude: Integer
MI History
  SSN/Patient ID: Text(11)
  Date/Time: Date/Time
  Q1: Text(200)
  Q2$a$: Byte
  Q2$b$: Byte
  Q3: Date/Time
  Q4: Byte
  Q5: Text(200)
  Q6$a$: Yes/No
  Q6$b$: Text(25)
  Q6$c$: Byte
  Q7$a$: Yes/No
  Q7$b$: Text(25)
  Q7$c$: Byte
  Q8$a$: Yes/No
  Q8$b$: Yes/No
  Q8$c$: Yes/No
  Q8$d$: Yes/No
  Q8$e$: Yes/No
  Q8$f$: Byte
  Q9$a$: Yes/No
  Q9$b$: Text(25)
  Q10$a$: Byte
  Q10$b$: Text(200)
  Q11$a$: Byte
  Q11$b$: Text(200)
  Q11$c$: Date/Time
  Q12: Date/Time
  Q13$a$: Yes/No
  Q13$b$: Byte
  Q13$c$: Byte
  Q14$a$: Yes/No
  Q14$b$: Byte
  Q14$c$: Date/Time
  Q15$a$: Yes/No
  Q15$b$: Date/Time
  Q16$a$: Yes/No
  Q16$b$: Text(200)
  Q17$a$: Yes/No
  Q17$b$: Text(200)
  Q18$a$: Yes/No
  Q18$b$: Text(200)
  Q19$a$: Yes/No
  Q19$b$: Yes/No
  Q19$c$: Yes/No
  Q19$d$: Yes/No
  Q19$e$: Yes/No
  Q20$a$: Yes/No
  Q20$b$: Yes/No
  Q20$c$: Yes/No
MI Pulse
  SSN/Patient ID: Text(11)
  Date/Time: Date/Time
  Carotid Pulse Left: Text(3)
  Carotid Pulse Right: Text(3)
  Brachial Pulse Left: Text(3)
  Brachial Pulse Right: Text(3)
  Abd Aorta Pulse: Text(3)

Femoral Pulse Left: Text(3)
Femoral Pulse Right: Text(3)
POP Pulse Left: Text(3)
POP Pulse Right: Text(3)
DP Pulse Left: Text(3)
DP Pulse Right: Text(3)
PT Pulse Left: Text(3)
PT Pulse Right: Text(3)
Carotid Bruits Left: Yes/No
Carotid Bruits Right: Yes/No
Abd Aorta Bruits: Yes/No
Femoral Bruits Left: Yes/No
Femoral Bruits Right: Yes/No
Carotid Doppler Signal Left: Integer
Carotid Doppler Signal Right: Integer
Brachial Doppler Signal Left: Integer
Brachial Doppler Signal Right: Integer
Femoral Doppler Signal Left: Integer
Femoral Doppler Signal Right: Integer
POP Doppler Signal Left: Integer
POP Doppler Signal Right: Integer
DP Doppler Signal Left: Integer
DP Doppler Signal Right: Integer
PT Doppler Signal Left: Integer
PT Doppler Signal Right: Integer
Lower Extremity Eval: Yes/No
Lower Extremity Eval Date: Date/Time In the current embodiment, the RigiScan function 872 is currently input as keypad entry data. However, in the future, it will be possible to provide an electronic port through an RS232 electronic linkage such that data compiled by a portable RigiScan device can be electronically downloaded into the RigiScan function 872.

In addition to the foregoing, the following tables identify electronic storage areas for medical forms, institution information and SVCR curves.

Medical Forms
    Med Form Code: Text(15)
    Med Form Sequence: Byte
    Med Form Full Name: Text(70)
    Med Sub Link Child: Text(50)
    Med Sub Link Parent: Text(50)
    Med Label: Text(50)
Institution
    Name: Text(100)
    Address: Text(50)
    City: Text(50)
    State: Text(50)
    Zip: Text(10)
    Phone: Text(12)
    Fax: Text(12)
    Stenographer: Text(50)
SVCR Curve
    SVCR: Double
    Venous Evaluation Points V2: Double As used herein, the term "database" is a set of interrelated files that is created and managed either by a database management system or the "database" is simply an electronically stored collection of data. All of this data, whether keypad entry data or digital instrument data signals (that is, the data signals obtained by the medical instruments which are converted into digital format), is interrelated based upon the entity relationship diagram shown in FIG. 14 and as further identified in the tables discussed herein. Since a database is utilized to interrelate and collect all this electronic data, it is also known that a spreadsheet could be utilized. As used herein, the term "database" includes a database as managed by a database management system, a spreadsheet and any other electronic linking of data.

Important features of the present invention are interrelation of the keypad entry data and the digital instrument data signals, enabling the technician to easily gather this data from the patient, and the production of vascular diagnostic reports without significant intervention by the technician. The reports are electronically generated based upon earlier acquired data.

FIGS. 15–39 diagrammatically illustrate vascular diagnostic reports compiled by the keypad entry data as well as the digital instrument data. These reports are generally standard in the industry, however, the present invention is the first device which integrates and generates these reports based upon a database compilation of keypad entry data and digital instrument data signals.

FIGS. 15–18 provide an arterial evaluation of the lower extremities utilizing the integrated peripheral vascular diagnostic system. As shown in FIG. 15, patient identification is shown in the upper region of the electronic form which is displayed to the technician on monitor 73. Other keypad entry data is obtained from the patient and logged into the vascular history portion of the report on FIG. 15. The arterial pulse data is keypad entry data obtained by the technician and entered via RCD 41. The doppler signals and the check marks on the lower region of the report indicate that the technician believes that those ultrasonic doppler signals are proper. When the technician prepares this report as discussed earlier herein, the technician could be wearing headphones 61 and listen to the doppler signals. It is an important feature of the present invention to visually present both the electronic version of this report shown in FIG. 15 as well as to enable the technician or the examining physician to listen to the doppler signals via headphones 61 at the same time as he or she looks at the electronic report. Of course, the vascular diagnostic report can be printed in color on printer 79 at the same time as the physician or technician listens to the doppler signal on headphones 61.

Figure 16:
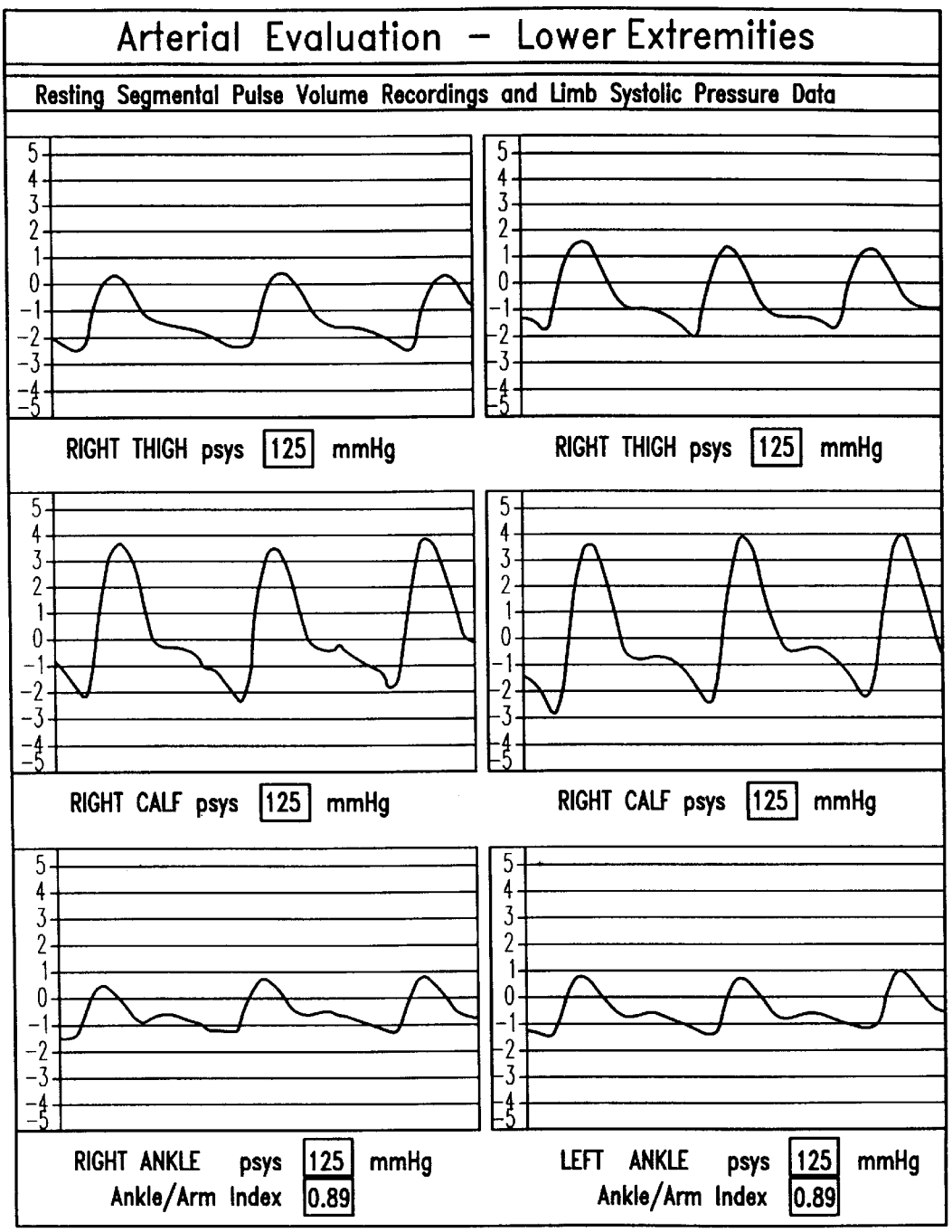
Figure 17:
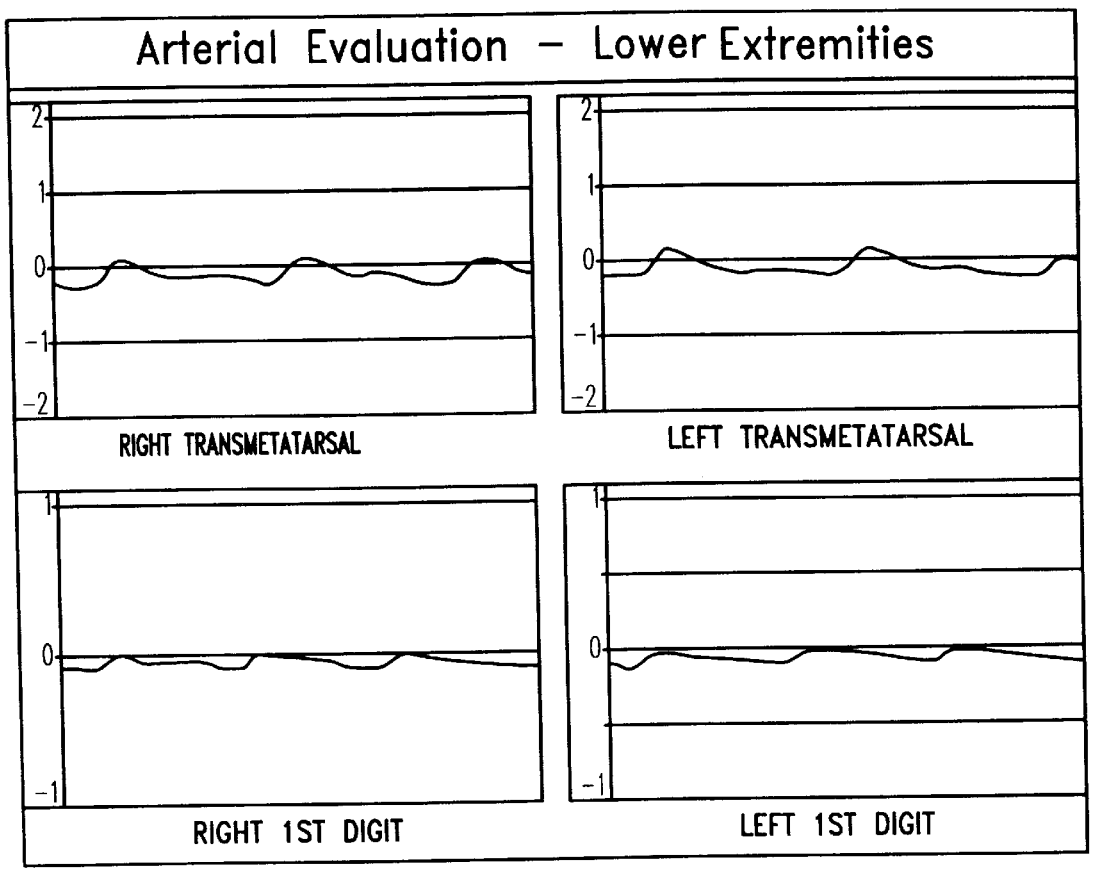

FIG. 16 shows a vascular diagnostic report revealing a printed out version of the analog signal obtained by the PVR. FIG. 17 also shows a printed out version of the analog signal. Of course, the electronic digital instrument data signal corresponding to this printout of the analog signal are electronically stored and linked with the electronic version of this report in the analysis unit 12.

Currently, at the end of the vascular examination by examining unit 10, the data is electronically transferred to computer system 16 of analyzing unit 12. By providing both the electronic version of the signals displayed in FIG. 17, with the printed out copy as well as the electronic form copy, the referring physician can further study the vascular condition of his or her patient.

FIG. 18 diagrammatically illustrates not only keypad entry data involving the exercise evaluation but also analog data showing PVR signals after the exercise.

Figure 19:
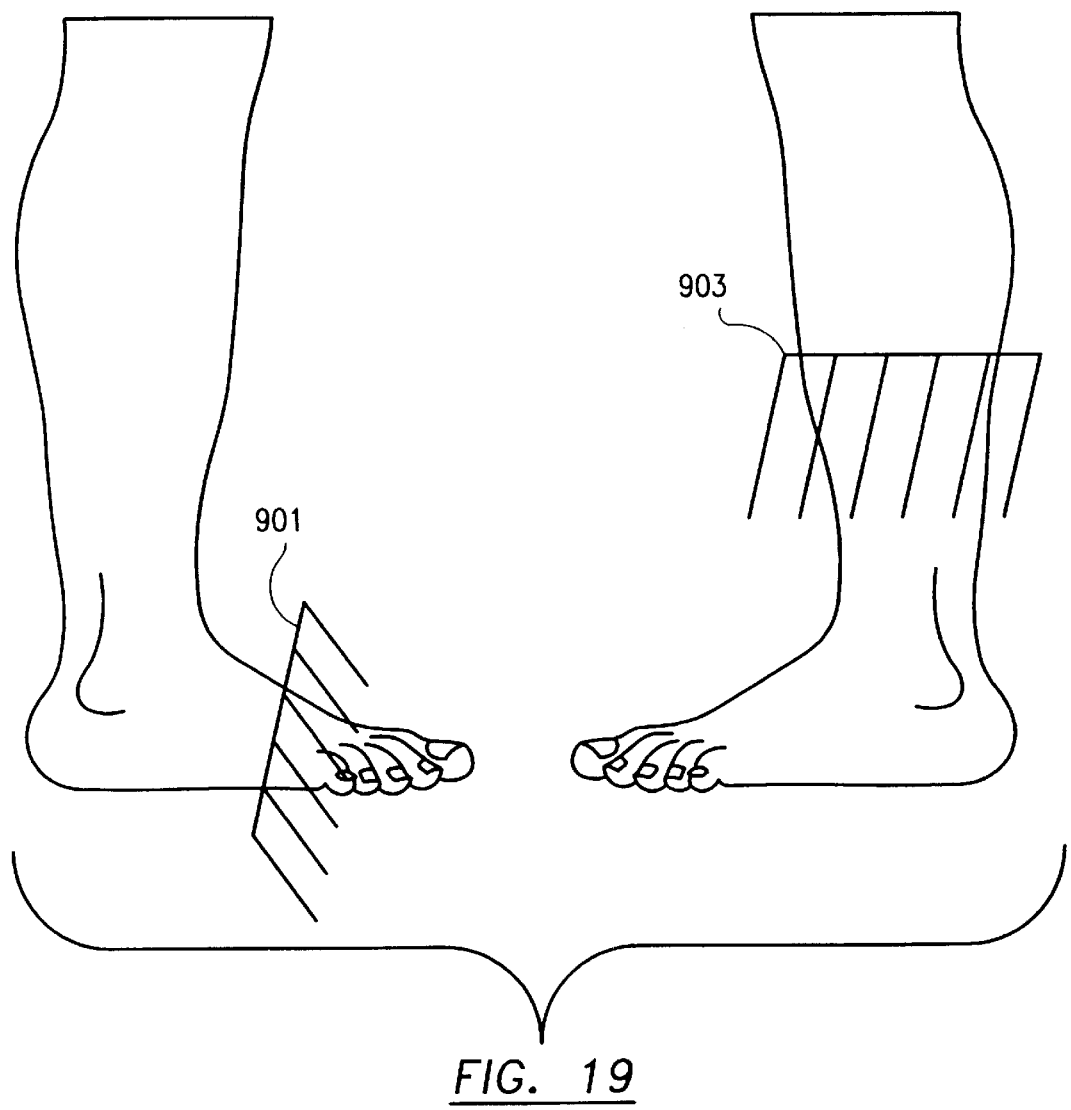

FIG. 19 diagrammatically illustrates how the record can be altered by showing an amputation. The pitchfork lines 901 and 903 can be moved by the technician during the preparation of the report. This is done by click and point and the particular software on the analysis unit. Accordingly, the technician or other physician can annotate the electronic record simply by moving symbols 901 and 903 to any point on either of the left or right legs.

Figure 20:
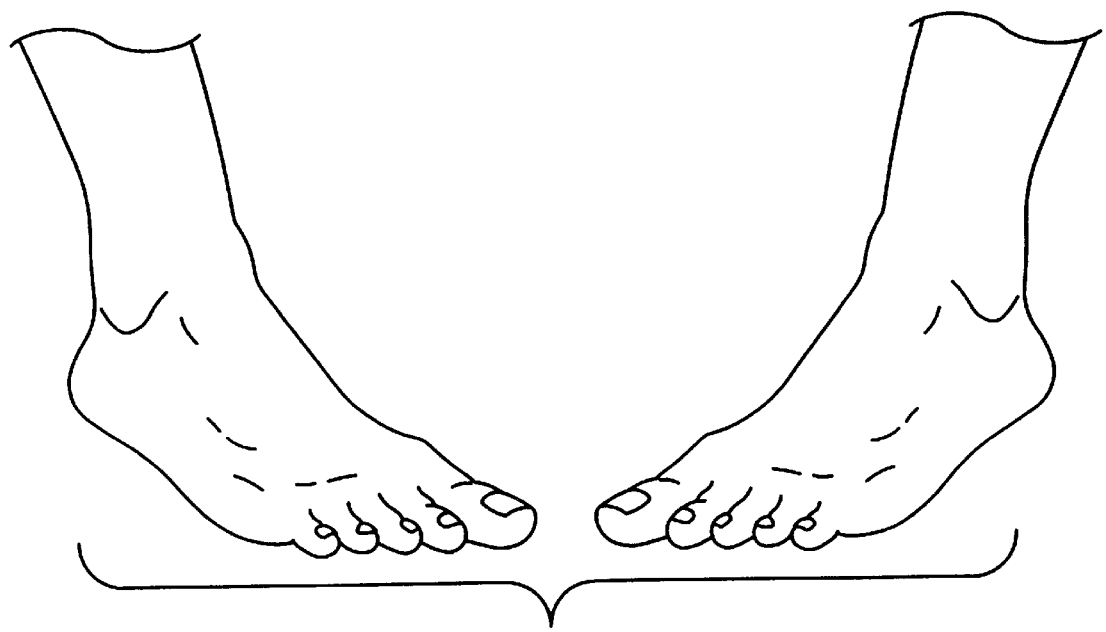

FIG. 20 shows the ability of the technician or physician to further annotate the electronic record by identifying lesions or other items on the graphic representations of the left and right foot.

Figure 21:
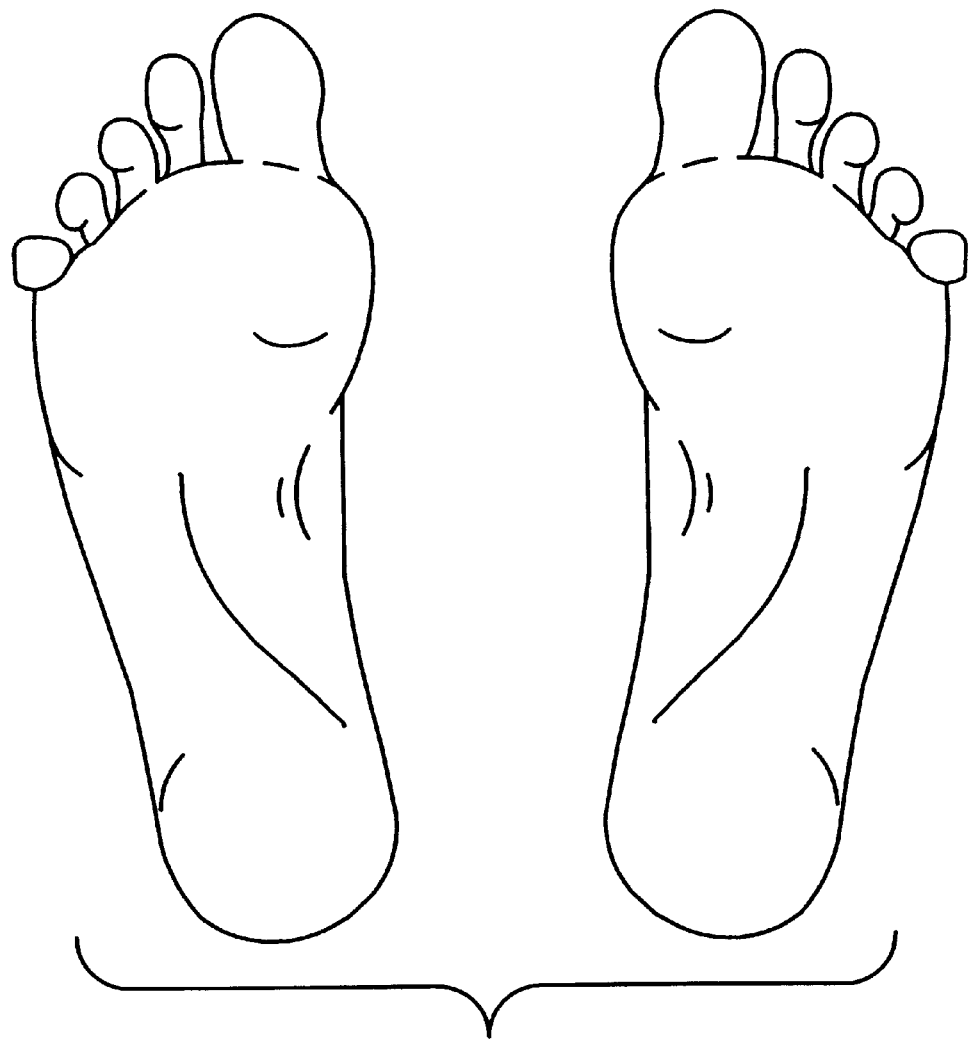

FIG. 21 provides another graphic representation of the foot which can be analyzed by analysis unit 12.

Figure 22:
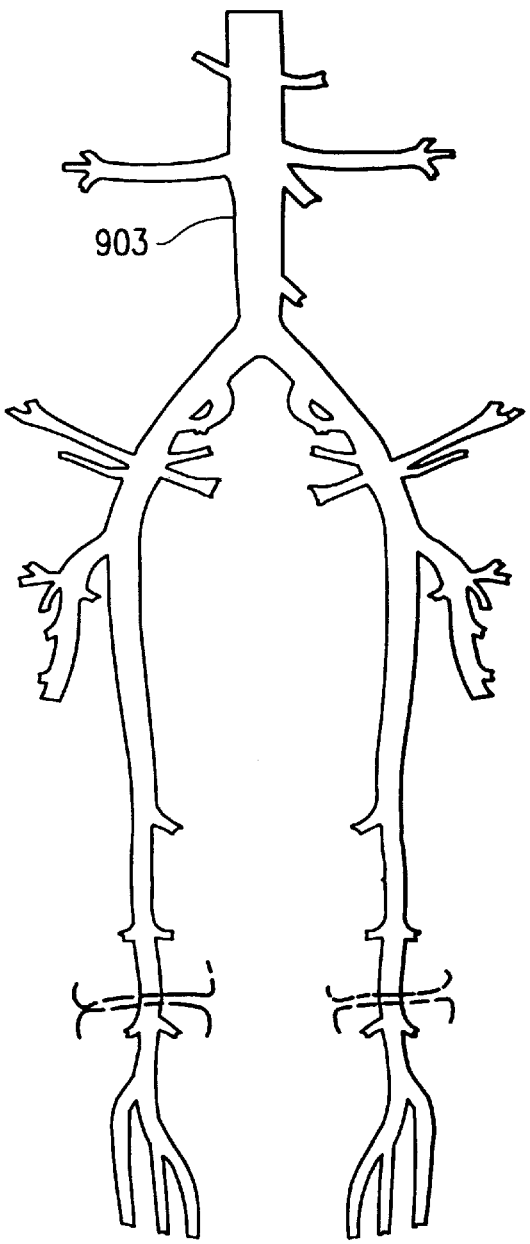

FIG. 22 diagrammatically illustrate the arterial evaluation of lower extremities. The technician or physician can move the residual lumen/calcification symbol, the soft plaque symbol, the smooth margins symbol, the irregular margins symbol, the ulceration margins symbol and the absorption symbol to any location on the graphic representation 903 of the vein or artery. In this manner, the electronic record can be amplified and annotated based upon the particular findings noted by the technician during the vascular exam.

Figure 27:
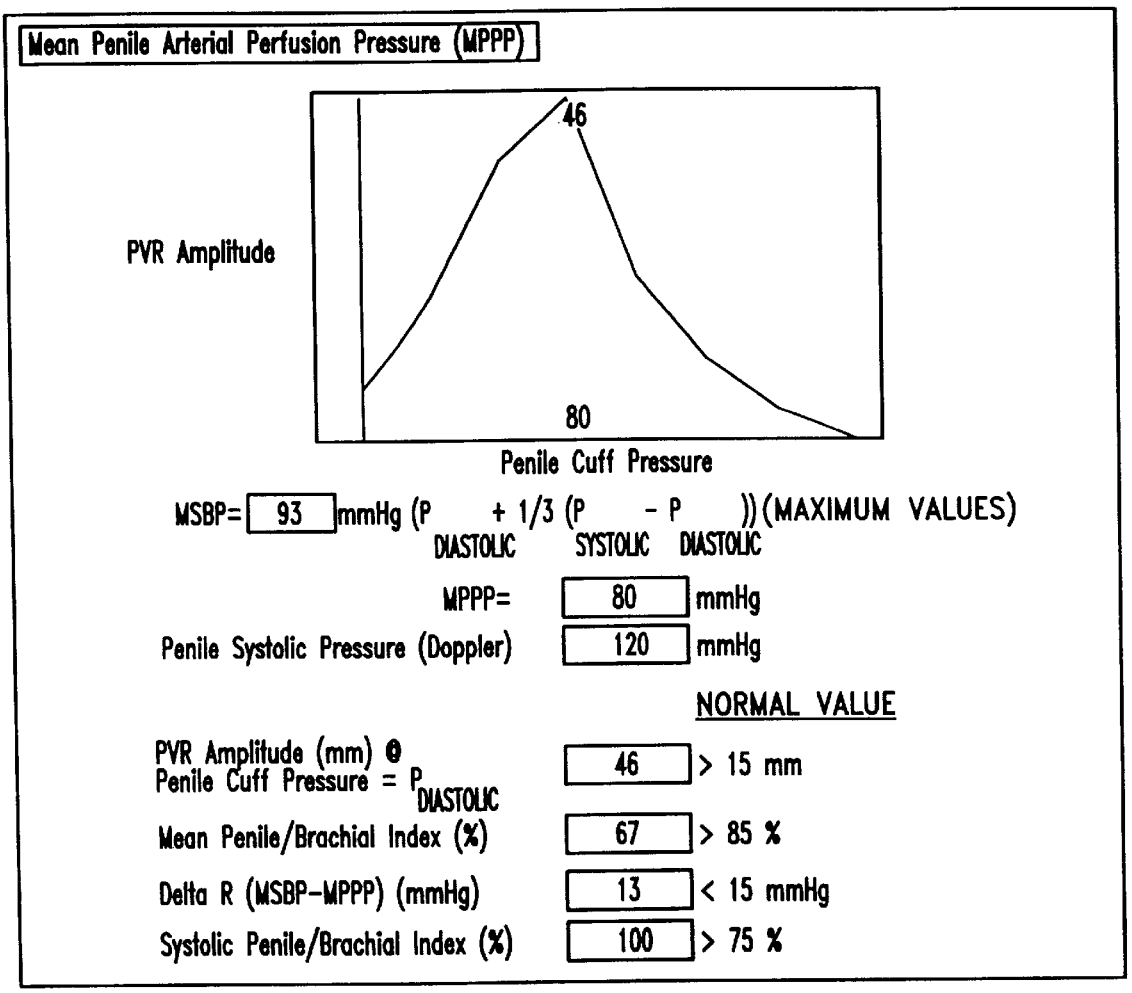

FIGS. 23–30 diagrammatically illustrate the electronic output forms for vascular diagnostic report involving male impotence MI. FIGS. 23, 24 and 25 diagrammatically illustrate keypad entry data in a form that can be used as part of a vascular analysis of male impotence. FIG. 26 is a graphic representation showing the keypad entry data from the technician as well as an indication that certain ultrasound doppler signals were obtained and considered normal by the technician. FIG. 27 graphically illustrates the mean penile arterial perfusion pressure which is a PVR analog signal. Further data, either keypad entry data or data calculated based on certain PVR values, are shown in FIG. 27. FIG. 28 is a biothesiometry table correlating vascular analysis of the fingers, the penis and the glans.

FIG. 29 represents the vascular diagnostic report for a RigiScan data. As discussed earlier, this data could be keypad entry data or could be electronically downloaded from a RigiScan device. The serum evaluation is keypad entry data which is based upon an analysis of the semen of the male patient.

Figure 30:
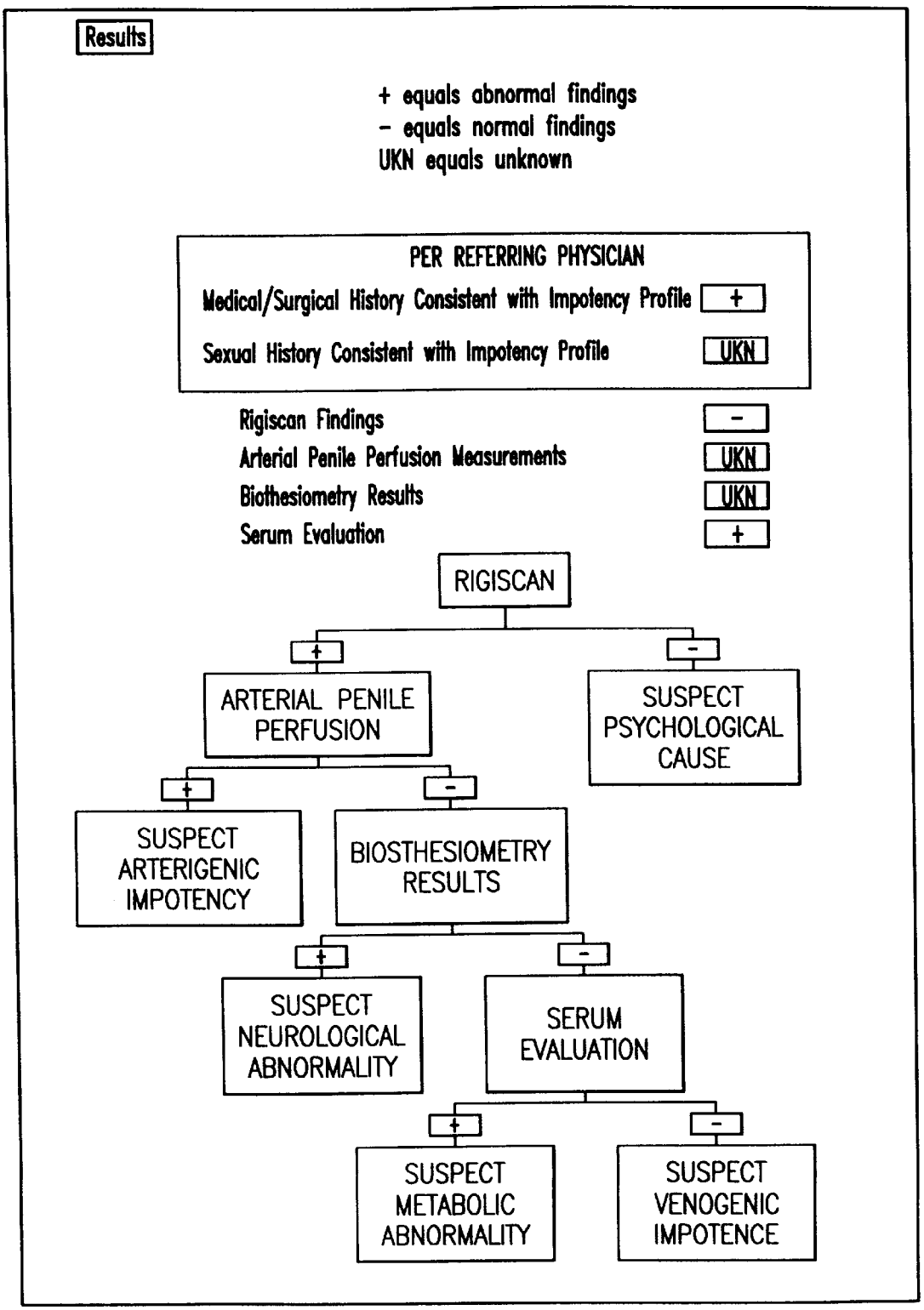
Figure 32:
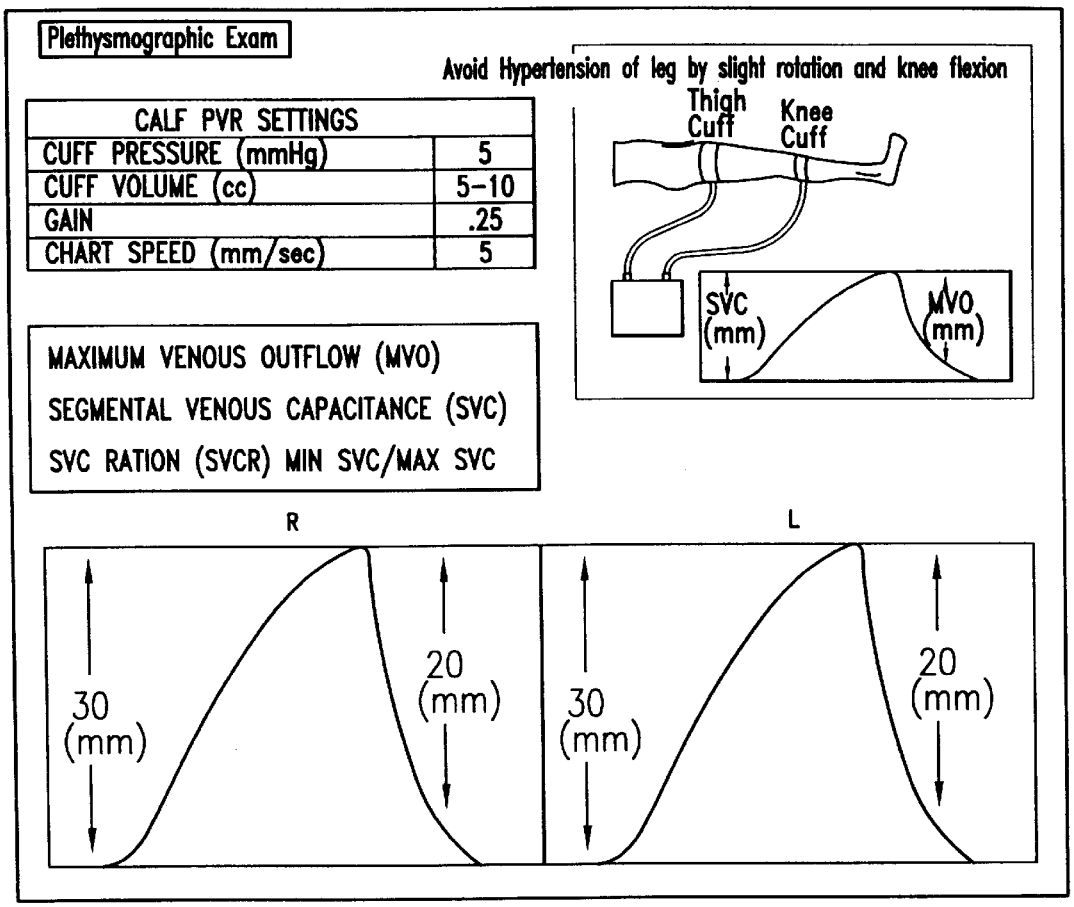
Figure 33:
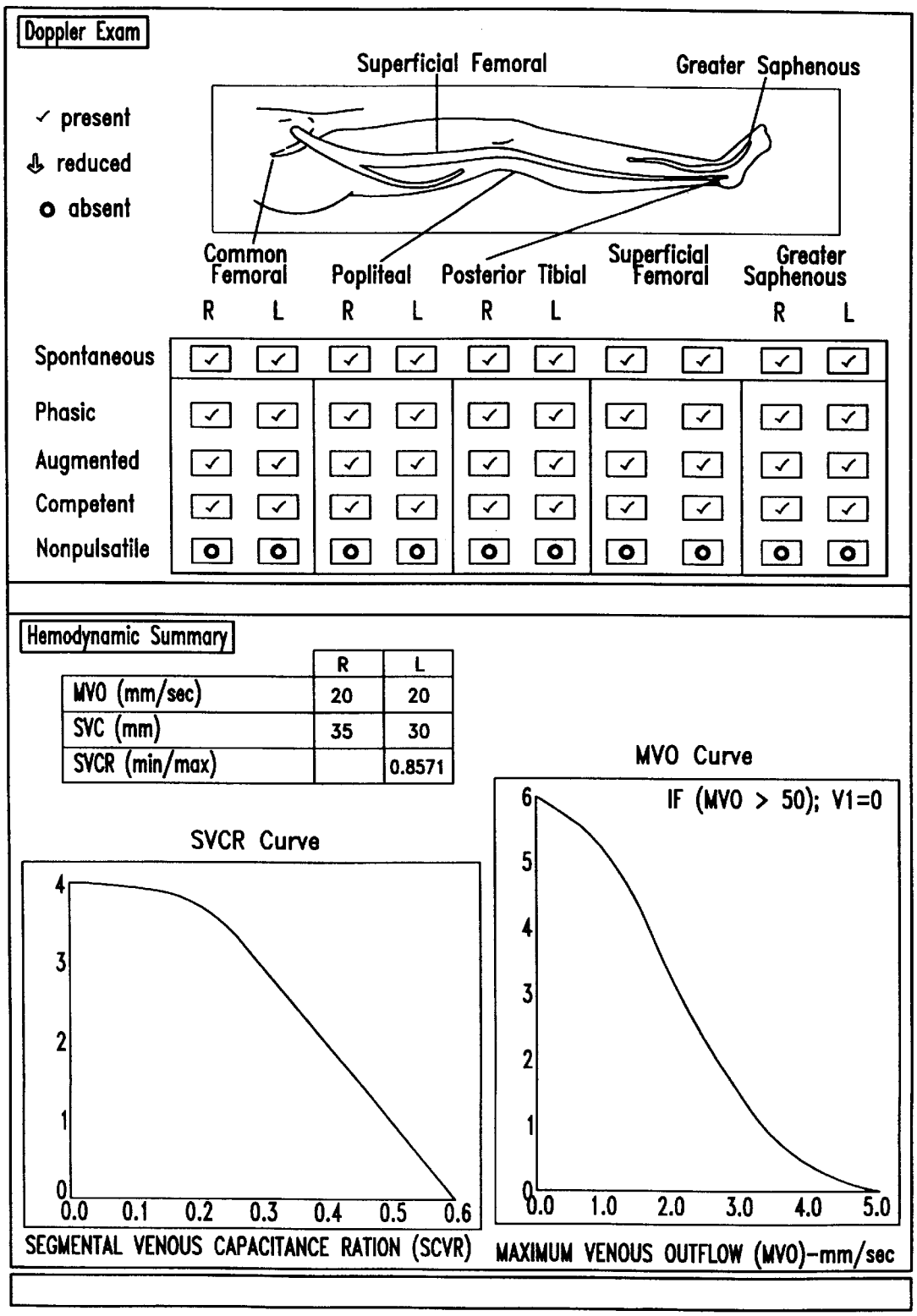

FIG. 30 presents a graphical representation providing an initial vascular analysis of the male impotence. Abnormal findings are indicated with a plus sign, normal findings are indicated by a negative sign, and UKN indicates unknown. FIGS. 31–34 diagrammatically illustrate a venous evaluation of lower extremities. FIG. 31 shows generally keypad entry data. FIG. 32 shows not only the data for the machine setting but also analog data representing a PVR recording. FIG. 33 shows the ultrasound doppler exam and an indication by the technician whether that doppler exam was present, reduced or absent. The hemodynamic summary shows analog representations of the SCVR curve and the MVO curve.

FIG. 34 shows a venous evaluation point.

Figure 35:
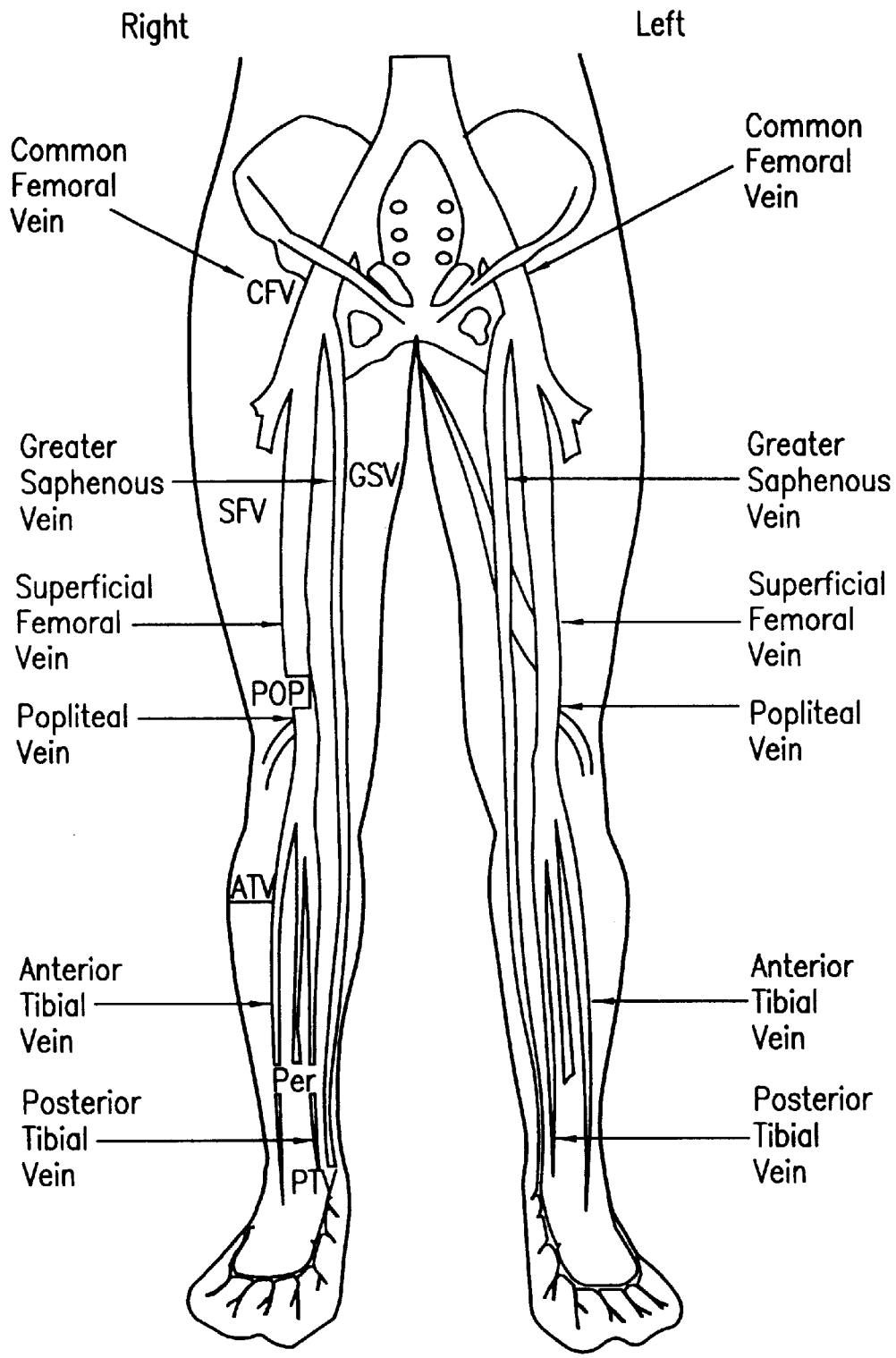

FIG. 35 is associated with the venous evaluation. The technician can annotate the graphic representation shown in FIG. 35 to indicate any problems.

FIGS. 36–39 relate to the carotid evaluation. FIG. 36 shows keypad entry data involving patient information, vascular history as well as a pulse analysis for the brachial blood pressure. FIG. 37 shows the OPG contraindications that the technician must complete prior to initiating the OPG test. If one of the indications is identified by the technician, the vascular diagnostic system will not permit the OPG test. Since no contraindications were indicated, the technician obtained the instrument data from the OPG. FIG. 37 shows the printed out analog version of the ophthalmic artery pressure.

Figure 39:
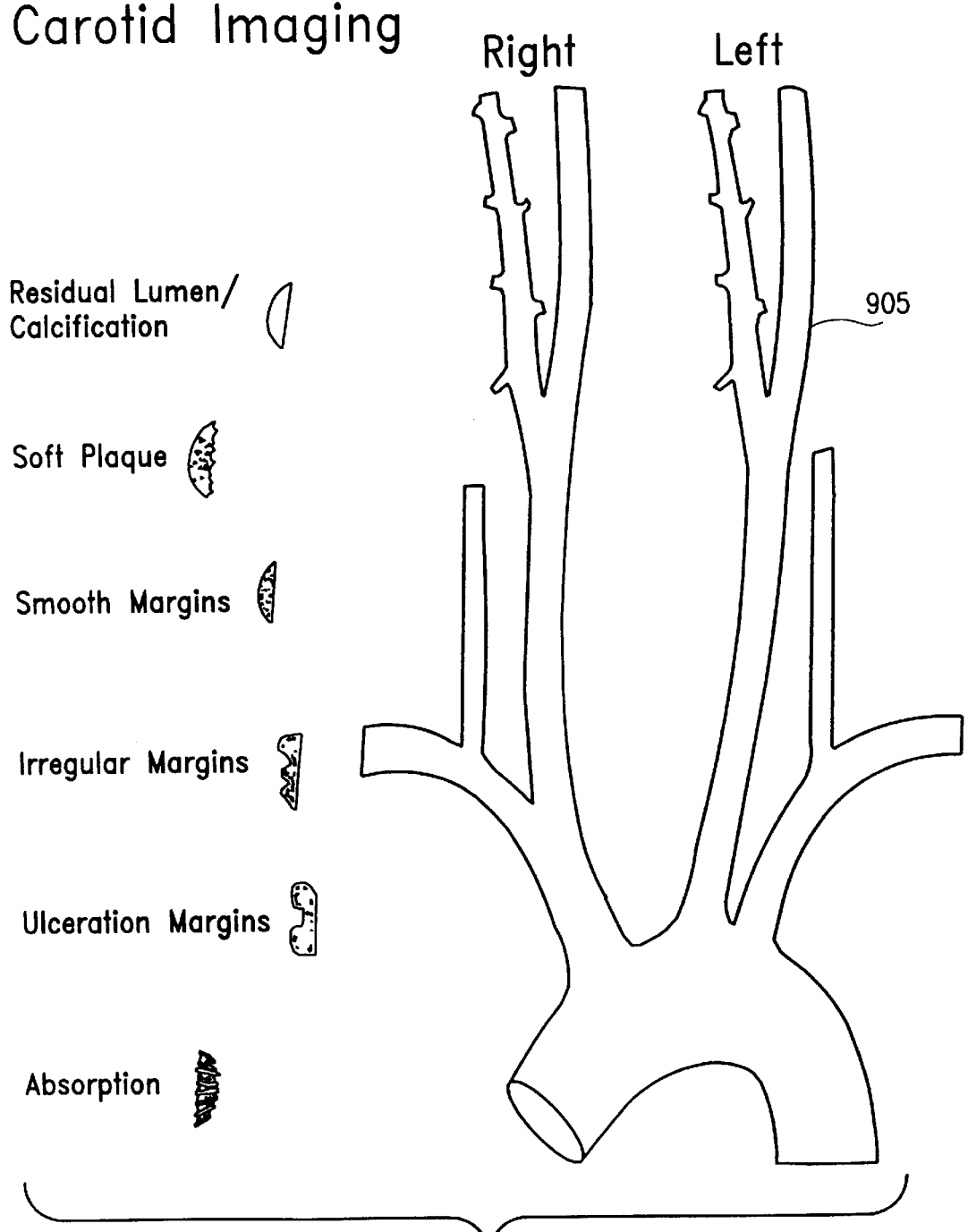

FIG. 38 shows a carotid audio frequency analysis CAA. When viewing this electronic form, the technician could select a playback button and listen to the audio frequency as actually recorded during the exam. The lower portion of FIG. 38 shows the continuous wave doppler exam results. FIG. 39 graphically shows a carotid artery. The technician, in compiling his or her vascular diagnostic report, could move the symbols for residual lumen/calcification, soft plaque, smooth margins, irregular margins, ulceration margins and absorption to any location on the carotid artery image 905. When stored with the recorded vascular form, that carotid image could be transferred to the referring physician for his or her further review.

Other forms could be utilized with the integrated peripheral vascular diagnostic system. The forms identified and discussed herein are exemplary in nature.

Figure 40:
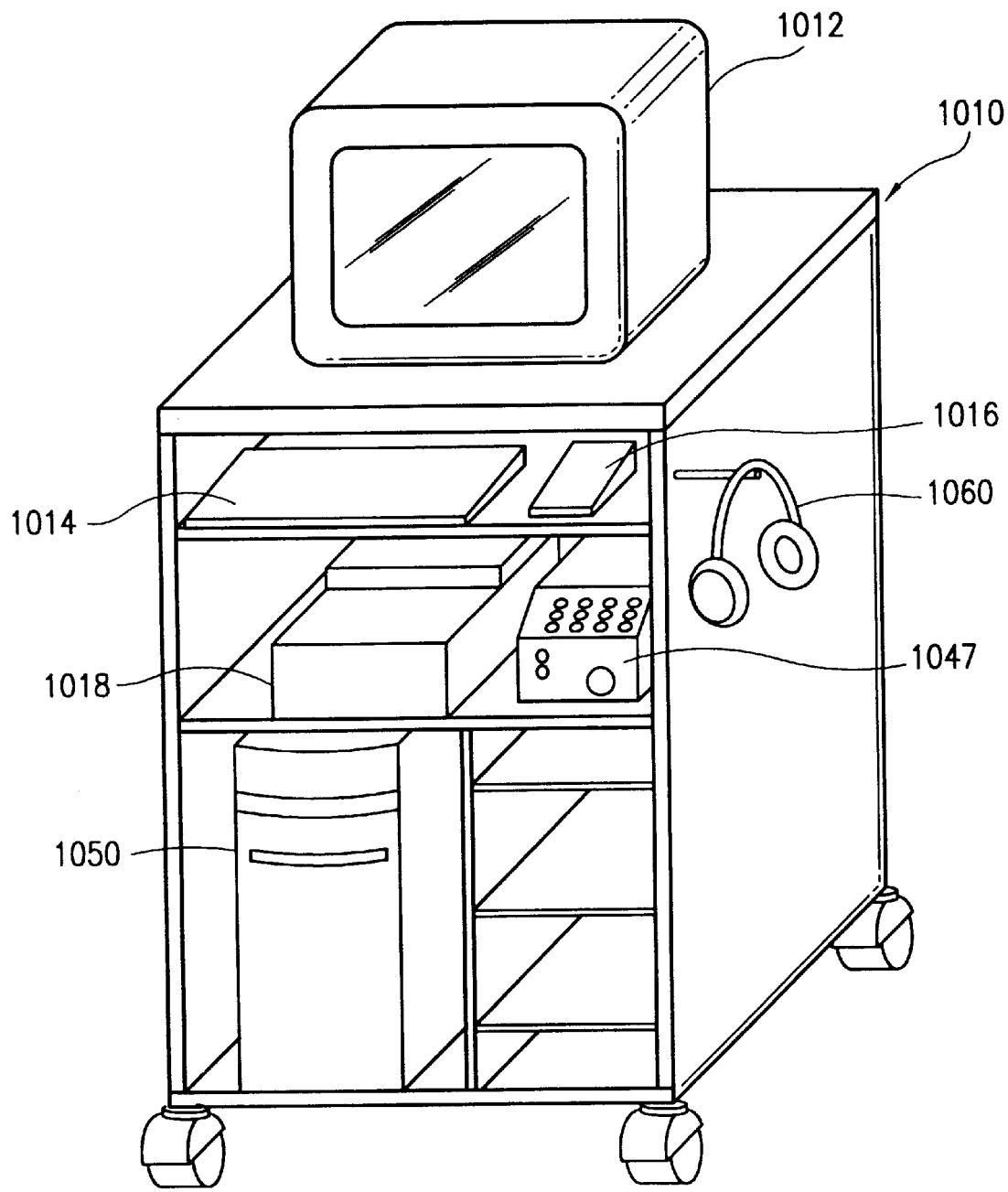
FIG. 40 diagrammatically illustrates another embodiment of the present invention wherein the integrated peripheral vascular diagnostic system utilizes a single computer and is placed on a cart.

FIG. 40 diagrammatically illustrates the integrated vascular diagnostic system on a cart 1010. Monitor 1012 is on the top of the cart. A keyboard 1014 and a remote control device 1016 are on the first shelf. On the second shelf, a color printer 1018 and a test port panel 1047 is located. As discussed earlier in connection with FIG. 1 and the other figures, various pressure cuffs, doppler probes, microphones, and other equipment can be plugged into test port panel 1047. The computer system 1050 can prompt the technician to gather vascular data. When the vascular exam is completed, the technician can analyze that data using keyboard 1014 and a mouse or track ball (not shown in FIG. 40). Headphones 1060 can be utilized to play back and listen to the doppler ultrasound signals as well as the audio frequency sound signals. Printed reports can be provided by printer 1018. As is known, the electronic version of the reports could be downloaded from computer system 1050 into a larger computer system for further study by the referring physician or another vascular physician.

The claims appended hereto are meant to cover modifications and changes within the spirit and scope of the present invention.

What is claimed is:

1. An integrated, peripheral vascular diagnostic system electronically linking a doppler ultrasound unit generating ultrasound doppler data signals and at least one from the group consisting of a pulse volume recorder (PVR), an ocular pneumoplethysmograph (OPG), a photoplethysmograph (PPG), and an audio frequency analysis (AA) unit, each respectively generating PVR, OPG, PPG, and AA data signals, the integrated diagnostic system comprising:

means for electronically acquiring and converting said doppler data signals into an initial set of digital data signals;

a computer system including a processor, a memory, a keypad input device, a display monitor, a printer and means for interfacing together said processor, said memory, said keypad, said display monitor, said printer and said means for acquiring and converting said data signals;

a data compilation means, incorporated into said computer system, for compiling and initially storing said initial set of digital data signals and patient data into said memory substantially concurrently with the acquisition of said doppler data signals, said patient data entered into said computer system via said keypad;

a report generator means, as part of said computer system, for generating at a time subsequent to the initial storage of said initial set of digital data signals and not during data acquisition, and displaying at said time subsequent, and printing at said time subsequent, a plurality of vascular diagnostic reports based upon said digital data signals and said patient data;

an analog playback means, as part of said report generator means, for presenting a visual analog version of at least some of said initial set of digital data signals and an audio analog version of at least some of said initial set of digital data signals; and, means for selecting, during the presentation, a portion of said stored initial set of digital data signals to be included in said vascular diagnostic report.

2. An integrated vascular diagnostic system as claimed in claim 1, wherein said respective data signals are instrument data signals, and said system includes means for converting said instrument data signals into further digital data signals and displaying, selecting and printing selected portions of the further digital data signals via said report generator means.

3. An integrated vascular diagnostic system as claimed in claim 1, wherein said report generator means includes means for storing said vascular diagnostic report with said selected portion of digital data signals.

4. An integrated vascular diagnostic system as claimed in claim 1, wherein said data signals are instrument data signals representing a plurality of waveforms, said means for acquiring and converting generating further digital data signals based thereon and representing corresponding waveforms, and said report generator means includes means for converting said initially stored digital data signals and further digital data signals into analog displays of said corresponding waveforms.

5. An integrated vascular diagnostic system as claimed in claim 1, wherein said playback means includes an audio system for listening to said analog version of said doppler data signals represented in part by said digital data signals during the display of said diagnostic reports by said report generator means.

6. An integrated vascular diagnostic system as claimed in claim 2, wherein said audio system includes one of headphone set and a speaker.

7. An integrated vascular diagnostic system as claimed in claim 1, wherein said data compilation means includes a data base manager program.

8. An integrated vascular diagnostic system as claimed in claim 2, wherein said playback means includes an audio system for listening to an analog version of said digital data signals and said further digital data signals.

9. An integrated vascular diagnostic system as claimed in claim 8, wherein said audio system includes a headphone set and said headphone set includes a radio frequency (RF) receiver, and said playback means includes means for transmitting said analog version of said digital data signals or said further digital data signals to said RF receiver.

10. An integrated vascular diagnostic system as claimed in claim 1, wherein said computer system includes a network port for enablement of a telecommunications link and a transfer of said digital data and said keypad entry data.

11. An integrated vascular diagnostic system as claimed in claim 9, wherein said computer system includes a network port for enablement of a telecommunications link and a transfer of said digital data and said keypad entry data.

12. An integrated vascular diagnostic system as claimed in claim 11, wherein said report generator and said means for selecting portions of said digital data signals includes means for reorganizing data into a plurality of electronic output forms, said report generator displaying and printing analog representations of said selected digital data and said reorganized data as said plurality of output forms.

13. An integrated vascular diagnostic system as claimed in claim 1, wherein said system includes a cart which carries said computer system.

14. An integrated vascular diagnostic system as claimed in claim 1, wherein said means for selecting includes means for scrolling through said stored initial set of digital data.

15. An integrated vascular diagnostic system as claimed in claim 2, wherein said means for selecting includes means for scrolling through said further digital data signals.

16. An integrated vascular diagnostic system as claimed in claim 1, wherein said system includes means for prompting the acquisition of at least one of said doppler data signals and said respective data signals, said means for prompting incorporated into said computer system and operative in conjunction with said display monitor.

17. An integrated, peripheral vascular diagnostic system utilizing patient data and electronically linking a doppler ultrasound unit generating ultrasound doppler data signals and at least one from the group consisting of a pulse volume recorder (PVR), an ocular pneumoplethysmograph (OPG), a photoplethysmograph (PPG), and an audio frequency analysis (AA) respective unit, each respectively generating PVR, OPG, PPG, and AA data signals, at least one of said doppler data signals and said respective data signals having an audio characteristic, the integrated diagnostic system comprising:

means for electronically acquiring and converting said data signals into an initial set of digital data signals;

a computer system including a processor, a memory, a keypad input device, a display monitor, a print unit and means for interfacing together said processor, said memory, said keypad, said display monitor, said print unit and said means for acquiring and converting said data signals;

a data compilation means, incorporated into said computer system for compiling and initially storing said initial set of digital data signals and said patient data into said memory;

a report generator means, as part of said computer system, for generating at a time subsequent to the initial storage of said initial set of digital data signals and not during data acquisition, displaying at said time subsequent, and printing at said time subsequent a plurality of vascular diagnostic reports based upon said digital data signals and said patient data;

an analog playback means, as part of said report generator means, for presenting both a visual analog version of at least some said initial set of digital data signals and an audio analog version of at least some of said initial set of digital data signals having said audio characteristic; and, means for selecting, during the presentation, a portion of said stored initial set of digital data signals to be included in said vascular diagnostic report.

18. An integrated vascular diagnostic system as claimed in claim 17, wherein said data signals include instrument data signals and doppler data signals, at least one of which has said audio characteristic, and said system includes means for linking the audio characteristic data signals with corresponding patient data and said selected portion of said digital data signals via said report generator means.

19. An integrated vascular diagnostic system as claimed in claim 17, wherein said doppler data signal has said audio characteristic and said analog playback means is utilized substantially concurrently with said means for selecting to store said selected portion of said data signal with said diagnostic report.

20. An integrated vascular diagnostic system as claimed in claim 18, wherein said instrument data signals include a plurality of waveforms, said digital data signals from said means for acquiring and converting represent corresponding waveforms based upon said instrument data signals, and said report generator means includes means for converting said corresponding initially stored digital data signals into analog displays and prints of said corresponding waveforms.

21. An integrated vascular diagnostic system as claimed in claim 17, wherein said playback means includes one of a speaker and a headphone set for listening to said analog version of said digital data or doppler data signals during the display of said diagnostic reports by said report generator means.

22. An integrated vascular diagnostic system as claimed in claim 17, wherein said print unit electronically prints and stores said diagnostic reports in said memory with said diagnostic report.

23. An integrated vascular diagnostic system as claimed in claim 21, wherein said playback means includes headphones and said headphones further include a radio frequency (RF) receiver, and said playback means includes means for transmitting said analog version of said digital data signals or doppler data signals to said RF receiver.

24. An integrated vascular diagnostic system as claimed in claim 17, wherein said computer system includes a network port for enablement of a telecommunications link and transfer of at least one of said digital data and said doppler data and said diagnostic report.

25. An integrated vascular diagnostic system as claimed in claim 20, wherein said report generator and said means for selecting portions of said initial set of digital data signals includes means for reorganizing said patient data and said selected portions of digital data signals into a plurality of electronic output forms, said report generator displaying and printing analog representations of said selected digital data and said patient data as said plurality of output forms.

26. An integrated vascular diagnostic system as claimed in claim 17, wherein said system includes a cart which carries said computer system.

27. An integrated vascular diagnostic system as claimed in claim 17, wherein said means for selecting includes means for scrolling through said stored initial set of digital data.

28. An integrated vascular diagnostic system as claimed in claim 18, wherein said means for selecting includes means for scrolling through said digital data signals.

29. An integrated vascular diagnostic system as claimed in claim 17, wherein said system includes means for prompting the acquisition of at least one of said doppler data signals and said respective data signals, said means for prompting incorporated into said computer system and operative in conjunction with said display monitor.

30. A method for electronically integrating a vascular diagnostic system by electronically linking patient data, a doppler ultrasound unit generating ultrasound doppler data signals and at least one from the group consisting of a pulse volume recorder (PVR), an ocular pneumoplethysmograph (OPG), a photoplethysmograph (PPG), and an audio frequency analysis (AA) unit, each respectively generating PVR, OPG, PPG, and AA data signals, the method comprising the steps of:

electronically acquiring and converting said doppler data signals into an initial set of digital data signals;

compiling and initially storing said initial set of digital data signals and said patient data into a data base, said initial storage of said initial set of digital data occurring substantially concurrently with the acquisition of said instrument data signals;

generating and displaying, at a time subsequent to said initial digital data storage and not during data acquisition, and printing a plurality of vascular diagnostic reports based upon said digital data signals and said patient data, at least a portion of said display and printing including the display and printing of analog representations of said digital data, the step of generating including the step of selecting a portion of said initial set of digital data representing said doppler data signals and subsequently storing said portion of digital data as part of said vascular diagnostic reports; and presenting both a visual analog version of at least some of said initial set of digital data signals and an audio analog version of at least some of said initial set of digital data signals substantially during the step of selecting.

31. A method as claimed in claim 30, including the step of audibly presenting analog representations of digital data substantially simultaneous with the visual display of said digital data.

32. A method as claimed in claim 31, including the step of reorganizing said patient data into a plurality of electronic output forms which represent said vascular diagnostic reports.

33. A method as claimed in claim 32, including the step of electronically transmitting said vascular diagnostic reports and said digital data outbound from said vascular diagnostic system.

34. A method as claimed in claim 30, including the step of scrolling through said initial set of digital data signals during the step of selecting.

35. A method as claimed in claim 30, including the step of prompting an input of at least one of said doppler data signals and said respective data signals.

36. A method as claimed in claim 30, including the step of audibly announcing said audio analog version of said initial set of digital data signals into an ambient environment during the step of presenting.

37. A method for electronically integrating a vascular diagnostic system by electronically linking a doppler ultrasound unit generating ultrasound doppler data signals and at least one from the group consisting of a pulse volume recorder (PVR), an ocular pneumoplethysmograph (OPG), a photoplethysmograph (PPG), and an audio frequency analysis (AA) unit, each respectively generating PVR, OPG, PPG, and AA data signals, at least one of said doppler data signals and said respective data signals having an audio characteristic, the method comprising the steps of:

electronically acquiring and converting said data signals into an initial set of digital data signals;

compiling and initially storing said initial set of digital data signals into a data base, said initial storage of said initial set of digital data occurring substantially concurrently with the acquisition of said instrument data signals;

generating and displaying, at a time subsequent to said initial digital data storage and not during data acquisition, and producing a plurality of vascular diagnostic reports based upon said digital data, at least a portion of said display including the display of analog representations of said digital data, the step of generating including the step of selecting a portion of said initial set of digital data, representing at least one of said doppler data and said respective data, and subsequently storing said portion of digital data as part of said vascular diagnostic reports; and presenting both a visual analog version of said initial set of digital data signals and an audio analog version of said initial set of digital data signals having said audio characteristic substantially during to the step of selecting.

38. A method as claimed in claim 37, including the step of audibly presenting analog representations of digital data simultaneous with the visual display of said digital data.

39. A method as claimed in claim 38, including the step of reorganizing said data into a plurality of electronic output forms which represent said vascular diagnostic reports.

40. A method as claimed in claim 39, including the step of electronically transmitting said vascular diagnostic reports and said digital data outbound from said vascular diagnostic system.

41. A method as claimed in claim 37, including the step of scrolling through said initial set of digital data signals during the step of selecting.

42. A method as claimed in claim 37, including the step of prompting an input of at least one of said doppler data signals and said respective data signals.

43. A method as claimed in claim 37, including the step of audibly announcing said audio analog version of said initial set of digital data signals having said audio characteristic into an ambient environment during the step of presenting.

\* \* \* \* \*